US006433012B1

(12) United States Patent
Tuse et al.

(10) Patent No.: US 6,433,012 B1
(45) Date of Patent: Aug. 13, 2002

(54) METHOD FOR INHIBITING INFLAMMATORY DISEASE

(75) Inventors: Daniel Tuse, Menlo Park; Charles Hiebert, Sunnyvale; Keith R. Laderoute; Nahid Waleh, both of Palo Alto, all of CA (US)

(73) Assignees: Large Scale Biology Corp., Vacaville, CA (US); SRI International, Menlo Park, CA (US)

( * ) Notice: Subject to any disclaimer, the term of this patent is extended or adjusted under 35 U.S.C. 154(b) by 0 days.

(21) Appl. No.: 09/656,144

(22) Filed: Sep. 6, 2000

Related U.S. Application Data

(63) Continuation-in-part of application No. 09/274,813, filed on Mar. 22, 1999, now Pat. No. 6,150,407.
(60) Provisional application No. 60/079,313, filed on Mar. 25, 1998.

(51) Int. Cl.[7] .............................................. A61K 31/12
(52) U.S. Cl. ...................... 514/532; 514/535; 514/543; 428/450
(58) Field of Search ............................... 514/532, 535, 514/543; 424/450

(56) References Cited

U.S. PATENT DOCUMENTS

| 4,994,443 A | * | 2/1991 | Folkman et al. | ............... 514/56 |
| 5,001,116 A | * | 3/1991 | Folkman et al. | ............... 514/56 |
| 5,013,556 A | * | 5/1991 | Woodle et al. | ............... 424/450 |
| 5,583,153 A | * | 12/1996 | Brahn | ........................ 514/449 |
| 5,736,576 A | * | 4/1998 | Kun et al. | |
| 5,922,775 A | * | 7/1999 | Kun et al. | ................... 514/685 |
| 6,017,958 A | * | 1/2000 | Kun et al. | |

FOREIGN PATENT DOCUMENTS

| WO | WO 95/29242 | * | 11/1995 | ............ C12N/15/57 |
| WO | WO 97/46228 | * | 12/1997 | ............ A61K/31/19 |
| WO | WO 99/20263 | * | 4/1999 | ............ A61K/31/12 |

OTHER PUBLICATIONS

Borrows, E.T., "The synthesis of thyroxine and related substances. Part I. The preparation of tyrosine and some of its derivatives; and a new route to thyroxine", *J. Chem. Soc.*, S185–190, (1949).*
Masuda, et al., "Thyroxine related compunds", *Takeda Kenkyusho Ho*, 30(3):466–474 (1971).*
Tripp, Spencer L., et al., "Synthesis of methylene– and carbonyl–bridge analogs of iodothyronines and iodothyroacetic acids", *J. Med. Chem.*, 16(1):60–64 (1973).*

Auerbach, et al., "A simple procedure for the long–term cultivation of chicken embryos", *Dev. Biol.*, 41:391–394 (1974).*
Taylor, et al., "Protamine is an inhibitor of angiogenesis", *Nature*, 297:307–312 (1982).*
Folkman, et al., "Angiogenesis inhibition and tumor regression caused by heparin or a heparin fragment in the presence of cortisone", *Science*, 221:719–725 (1983).*
Tracey, et al., "Anti–cachectin/TNF monoclonal antibodies prevent septic shock during lethal bacteraemia", *Nature*, 330:662–664 (1987).*
Maragoudakis, et al., "Antiangiogenic action of heparin plus cortisone is associated with decreased collagenous protein synthesis in the chick chorioallantoic membrane system", *J. Pharm. Exp. Ther.*, 251:679–682 (1989).*
Silva, et al., "Prophylactic and therapeutic effects of a monoclonal antibody to tumor necrosis factor–α in experimental gram–negative shock", *J. Infect. Dis.*, 162:421–427 (1990).*
Langer, Robert, ew methods of drug delivery, *Science*, 249:1527–1533 (1990).*
Williams, et al., "Anti–tumor necrosis factor amneliorates joint disease in murine collagen–induced arthritis", *Proc. Natl. Acad. Sci. USA*, 89:9784–9788 (1992).*
Waleh, et al., "Selective down–regulation of integrin receptors in spheroids of squamous cell carcinoma", *Cancer Res.*, 54:838–843 (1994).*
Jain, et al., "Quantitative angiogenesis assays: progress and problems", *Nat. Med.*, 3(11):1203–1208 (1997).*
Lin, et al., "Inhibition of tumor angiogenesis using a soluble receptor establishes a role for Tie2 in pathologic vascular growth", *J. Clin. Invest.*, 100(8):2072–2078 (1997).*
Mendeleyev, Jerome, et al., "Structural specificity and tumoricidal action of methyl–3, 5–diiodo–4–(4'–methoxyphenoxy) benzoate (DIME)", *Int. J. Oncol.*, 10(4):689–695 (1997).
Kun, Ernest, et al., "Molecular pharmacology of methyl–3, 5–diiodo–4 (4'methoxyphenoxy) benzoate (DIME) and its non–hydrolyzible ethanone analog (DIPE)* (Review)", *Int. J. Mol. Med.*, 2(5):585–590 (Nov. 11, 1998).
Chen, Xiaoying, et al., "Oncocidin A1: A novel tubulin–binding drug with antitumor activity against human breast and ovarian carcinoma xenografts in nude mide", *Biochem. Pharmacol.*, 56(5):623–633 (Sep. 1, 1998).

* cited by examiner

Primary Examiner—Frederick Krass
(74) *Attorney, Agent, or Firm*—Townsend and Townsend and Crew LLP

(57) ABSTRACT

The present invention relates to methods for effectively inhibiting inflammatory diseases, such as Crohn's disease and ulcerative colitis. In other aspects, this invention relates to methods of reducing or inhibiting granulomas.

20 Claims, 9 Drawing Sheets

METHOD FOR INHIBITING INFLAMMATORY DISEASE

This application claims priority to U.S. Provisional Patent Application No. 60/079,313, filed Mar. 25, 1998, and continuation-in-part of U.S. application Ser. No. 09/274,813, filed Mar. 22, 1999, now U.S. Pat. No. 6,150,407 the teachings of which are incorporated herein by reference in their entireties.

FIELD OF THE INVENTION

The present invention relates to methods for effectively inhibiting unwanted angiogenesis. More particularly, this invention relates to methods of treating diseases associated with unwanted angiogenesis and to delivering anti-angiogenic activity to mammals having such diseases.

BACKGROUND OF THE INVENTION

Angiogenesis is the development of new blood vessels from existing microvessels. The process of generating new blood vessels plays an important role in embryonic development, in the inflammatory response, in the development of metastases (tumor induced angiogenesis or TIA), in diabetic retinopathy, in the formation of the arthritic panus and in psoriasis. Under normal physiological conditions, humans or animals only undergo angiogenesis in very specific, restricted situations. For example, angiogenesis is normally observed in wound healing, in fetal and embryonal development and in the formation of the corpus luteum, endometrium and placenta. The control of angiogenesis is a highly regulated system involving angiogenic stimulators and inhibitors. The control of angiogenesis has been found to be altered in certain disease states and, in many cases, the pathological damage associated with the disease is related to the uncontrolled angiogenesis.

In tumor angiogenesis, for example, capillary sprouts are formed, their formation being induced by a group of tumor cells. However, compared with blood vessels produced in normal angiogenic microenvironments, tumor microvessels are morphologically and functionally unique. Their vascular networks typically show disorganized or aberrant architecture, luminal sizes vary and blood flow can fluctuate chaotically. There are two principal types of tumor angiogenesis in terms of the events that follow implantation of metastatic seedlings on surfaces and in organs. The first or primary angiogenesis is the initial vascularization of the mass of multiplying tumor cells and is regarded as an essential prerequisite for the survival and further growth of a metastatic deposit. The second is a continuing or secondary angiogenesis and is the phenomenon, which occurs in waves at the periphery of a growing tumor mass. This second angiogenesis is essential for the accretion of new microcirculatory territories into the service of the expanding and infiltrating tumor.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed to the control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Diseases associated with retinal/choroidal neovascularization include, but are not limited to, diabetic retinopathy, macular degeneration, sickle cell anemia, sarcoid, syphilis, pseudoxanthoma elasticum and Pagets disease.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that led to pannus growth and cartilage destruction.

An important area of current research in therapeutic oncology is focused on the discovery and development of anti-angiogenic agents that target tumor vasculature by inhibiting or suppressing new blood vessel growth. Several kinds of compounds have been used to prevent angiogenesis. For instance, Taylor, et al. have used protamine to inhibit angiogenesis (see, Taylor, et al., *Nature* 297:307 (1982)). However, the toxicity of protamine limits its practical use as a therapeutic. In addition, Folkman, et al. have disclosed the use of heparin and steroids to control angiogenesis (see, Folkman, et al., *Science* 221:719 (1983) and U.S. Pat. Nos. 5,001,116 and 4,994,443). Steroids, such as tetrahydrocortisol, which lack gluco- and mineral-corticoid activity, have been found to be angiogenic inhibitors. In addition, angiostatin proteins have been shown to reversibly inhibit proliferation of endothelial cells. Angiostatin is capable of inhibiting angiogenesis-related diseases and modulating angiogenic processes (see, e.g., WO 95/292420).

In view of the foregoing, it is apparent that there remains a need in the art for methods and compounds for inhibiting angiogenesis, either by competitively inhibiting an angiogenesis factor or by some other mechanism. Such methods and compounds would have an adverse effect on the growth of tumors and, in addition, could be used to treat many of the other diseases set forth above. The methods of the present invention fulfill this and other needs.

SUMMARY OF THE INVENTION

In one aspect, this invention relates to a method of inhibiting the vascularization of endothelial cells, the method comprising contacting a cell, tissue or organ which has endothelial cells with an anti-angiogenic amount of a compound of Formula I. Compounds of Formula I have the following general formula:

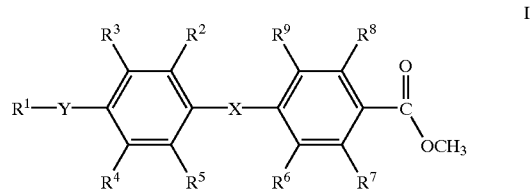

In Formula I, $R^1$ is a functional group including, but not limited to, $C_1$–$C_6$-alkyl.

In Formula I, $R^2$, $R^3$, $R^4$ and $R^5$ are each independently selected and are functional groups including, but not limited to, hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$ and $NH_2$.

In Formula I, $R^6$, $R^7$, $R^8$ and $R^9$ are each independently selected and are functional groups including, but not limited to, hydrogen, $C_1$–$C_6$-allyl, $C_2$–$C_6$-alkenyl, $C_2$–$C_6$-alkynyl, aryl, hydroxyl, $C_1$–$C_6$-alkoxy, halogen, $NO_2$ and $NH_2$.

In Formula I, X, if present, is a functional group including, but not limited to, the following: oxygen, sulfur, —$CH_2$—, or carboxy.

In Formula I, Y is a heteroatom including oxygen or sulfur.

In a preferred embodiment of the invention, the compound of Formula I is methyl-3,5-diiodo-4-(4'-methoxyphenoxy)benzoate ("BTO-956").

In another aspect, this invention relates to a method for effectively inhibiting unwanted angiogenesis in a tissue or organ, the method comprising contacting the cell with a compound of Formula I, or a pharmaceutical composition thereof, in an amount sufficient to inhibit angiogenesis. In a presently preferred embodiment, the cell is in a mammalian subject.

In yet another aspect, this invention relates to a method of treating mammalian diseases mediated by or associated with undesired and uncontrolled angiogenesis, the method comprising administering to a mammal an anti-angiogenic compound of Formula I in a dosage sufficient to inhibit angiogenesis. These methods are useful for ameliorating the effects of conditions that are characterized by abnormal or undesirable angiogenesis or endothelial cell proliferation.

In another aspect, this invention relates to methods that reduce the level of tumor necrosis factor a (TNF-α) produced by a cell.

In still yet another aspect, this invention relates to methods of using such compounds to reduce TNF-α production and to treat inflammatory diseases.

Other features, objects and advantages of the invention and its preferred embodiments will become apparent from the detailed description, which follows.

DETAILED DESCRIPTION OF THE INVENTION AND PREFERRED EMBODIMENTS

A. DEFINITIONS

Figure 1A:
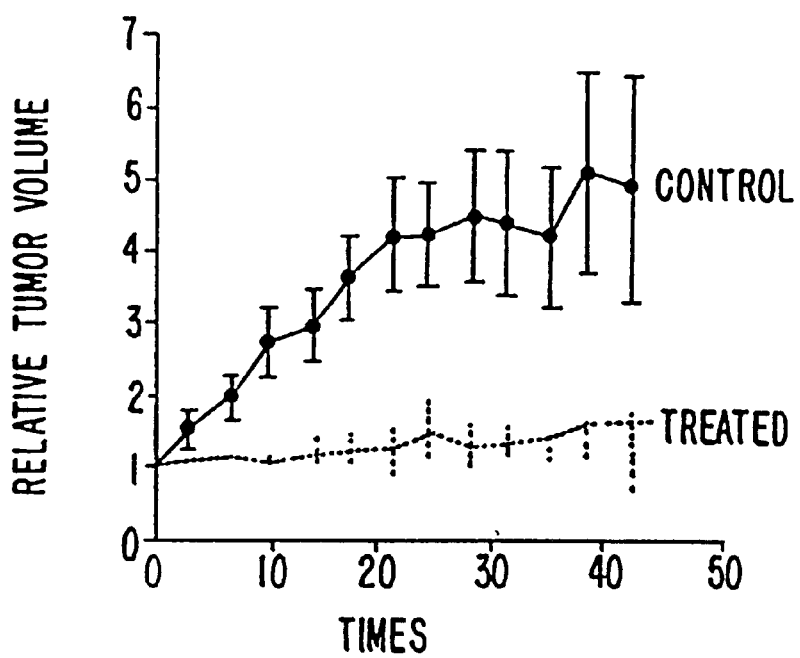
FIG. 1 illustrates the mean growth response as relative tumor volume of MDA MB-231 FIG. 1(A) and OVCAR3 FIG. 2(B) tumors in nude mice exposed to BTO-956.

The term "angiogenesis" refers to he generation of new blood vessels into cells, tissue, organs or tumors.

The term "metastasis." refers to the process by which tumor cells are spread to distant parts of the body. The term is also used herein to refer to a tumor that develops through the metastatic process.

The term "independently selected" is used herein to indicate that the R groups, e.g., $R^1$, $R^2$, $R^3$ and $R^4$, can be identical or different (e.g., $R^1$, $R^2$, $R^3$ and $R^4$ may all be hydrogens or $R^1$ and $R^4$ may be hydrogen and $R^2$ and $R^3$ may be halogen, etc.).

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamine, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "S-alkyl" is used herein to refer to the group -SR, where R is lower alkyl or substituted lower alkyl as defined herein.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

"Substituted aryl" refers to aryl as just described including one or more functional groups such as lower alkyl, acyl, halogen, alkylhalos (e.g. $CF_3$), hydroxy, amino, alkoxy, alkylamine, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "halogen" is used herein to refer to fluorine, bromine, chlorine and iodine atoms.

The term "hydroxy" is used herein to refer to the group —OH.

The term "amino" is used to refer to the group —NRR', where R and R' may independently be hydrogen, alkyl, substituted alkyl, aryl, substituted aryl or acyl.

The term "nitro" is used herein to refer to the group —$NO_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkenyl" is used herein to refer to an unsaturated branched, straight chain or cyclic monovalent hydrocarbon radical having at least one carbon-carbon double bonds. The radical can be in either the cis or trans conformation about the double bond(s). Suitable alkenyl radicals include, for example, ethenyl, propenyl, isopropenyl, cyclopropenyl, butenyl, isobutenyl, cyclobutenyl, tert-butenyl, pentenyl, hexenyl, etc.

The term "alkynyl" is used herein to refer to an unsaturated branched, straight chain or cyclic monovalent hydrocarbon radical having at least one carbon-carbon triple bond. Suitable alkynyl radicals include, for example, ethynyl, propynyl, butynyl, isobutynyl, pentynyl, hexynyl, etc.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

"An amount sufficient," "an effective amount," "therapeutically effective amount" or "anti-angeogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

B. THE COMPOUNDS

The present invention relates to the discovery that compounds of Formula I are useful for inhibiting angiogenesis and/or for treating angiogenic diseases. Compounds of Formula I have the following general formula:

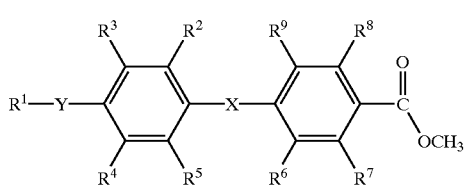

wherein $R^1$, $R^2$, $R^3$, $R^4$, $R^5$, $R^6$, $R^7$, $R^8$, $R^9$, X and Y are as defined above. In a preferred embodiment of the invention, the compound of Formula I is methyl-3,5-diiodo-4-(4'-methoxyphenoxy)benzoate ("BTO-956").

The compounds used in the methods of the current invention can be made in accordance with the procedure outlined in Borrows, et al., *J. Chem. Soc.* 1949, S185–190 and WO 97/46228, the teachings of which are incorporated herein by reference. In general, the process is accomplished in a series of steps. For instance, starting with the case of BTO-956, a substituted phenol and a substituted benzoate are reacted to yield methyl 3,5-dinitro-4-(4-methoxyphenoxy)benzoate. The nitro groups of the benzoate are then reduced to amines and subsequently replaced by iodine. This method for preparing BTO-956 is essentially as described in: Masuda, K., Imashiro, Y., and Okada, Y. "Synthesis of Triiodothyroformic Acid and its Derivatives," *J. Takeda Res. Lab.*, 1970, 29, 545–552, the teachings of which are incorporated herein by reference. Further synthetic details are set forth in Example 1.

Compounds suitable for use in the methods of the present invention can readily be identified using in vitro and in vivo screening assays. Such assays may screen for the ability of a particular compound to inhibit angiogenesis or the vascularization of endothelial cells in vitro and in vivo. For instance, the chick embryo chorioallantoic membrane (CAM) assay, which is described in more detail below, can be used to screen a given compound for its ability to inhibit vascularization. In the chorioallantoic membrane assay, fertilized chick embryos are removed from their shell on day 3 or 4, and a methylcellulose disc containing a compound of Formula I is implanted on the chorioallantoic membrane. The embryos are examined 48 hours later and, if a clear avascular zone appears around the methylcellulose disc, the diameter of that zone is measured. This assay can be used to assess the anti-angeogenic properties of the compounds of Formula I.

Another useful screening assay to assess the efficacy of compounds of Formula I is the corneal micropocket angiogenesis assay (CMA). The rat corneal micropocket assay can be used to assess the ability of compounds of Formula I to inhibit corneal angiogenesis (see, "Quantitative Angiogenesis Assays: Progress and Problems," *Nat. Med.*, 3: 1203–1208, 1997) and "Inhibition of Tumor Angiogenesis Using a Soluble Receptor Establishes a Role for Tie2 in Pathologic Vascular Growth," *J. Clin. Invest.*, 100: 2072–2078, 1997). In this assay, the compound of Formula I is mixed with a polymer (e.g., Hydron solution; Interferon Sciences, New Brunswick, N.J.) and implanted in a small pocket surgically created in the superficial layers of the cornea of a rat. Under normal circumstances, this wound stimulates an angiogenic response, which is readily visible as the appearance of neovessels on the normally avascular cornea. If the compound of Formula I is effective, specifically as an anti-angiogenic agent, it inhibits or block this response. In one experimental design, a group of five animals (including a control group with only polymer implants) is tested over a range of drug doses, which can induce tumor growth delay. Three doses are tested in the assay. Assessment of an anti-angiogenic response by this method is categorical. In other words, a treated eye is either positive or negative for corneal angiogenesis. This assay determines whether a compound of Formula I is directly anti-angiogenic in an in vivo mammalian model of angiogenesis.

In addition, the human microvascular endothelial cell assay (HMVEC) can be used to assess the efficacy of compounds of Formula I. HMVEC are seeded into a 96-well plate at a x concentration of $5 \times 10^3$ cells/well in a volume of 100 μl/well of Endothelial Growth Medium. Plates are then incubated at 37° C. in 5% $CO_2$ for 24 h and then aliquots of the compound of Formula I are added to the HMVEC preparations and plates are then incubated at 37° C. in 5% $CO_2$ for 3 days. The relative number of cells is determined by adding 20 μl/mL of Alamar Blue for 3–6 h at 37° C. and measuring color changes indicating metabolic activity by using a Fluorescence Measurement System. In this assay, the intensity of the fluorophore signal is directly proportional to cell number.

The HMVEC assay can also be carried out using human umbilical vein microvascular endothelial cells (HUMVEC). This assay is carried out similarly to the above assay, but HUMVEC cells are used. In addition, other assays known to those of skill in the art can readily be used to screen the compounds of the present invention for anti-angiogenic properties.

It will be readily apparent to those skilled in the art that the compounds of Formula I can be administered alone, in the form of a pharmaceutically acceptable salt and/or in the form of a pharmaceutical composition.

C. USES FOR THE COMPOUNDS OF THE PRESENT INVENTION

As explained above, the present invention relates to the discovery that the compounds of Formula I are useful for inhibiting angiogenesis and, in turn, for treating diseases associated with unwanted angiogenesis. As such, in one embodiment, the present invention provides a method of inhibiting unwanted angiogenesis in a cell, the method comprising contacting the cell with an effective amount, i.e., an anti-angiogenic amount, of a compound of Formula I. In another embodiment, the present invention provides a method of inhibiting the vascularization of endothelial cells, the method comprising contacting a cell, tissue or organ containing the endothelial cells with an effective amount of a compound of Formula I. In a presently preferred embodiment, the cells are in a mammalian subject.

This invention relates to a method of treating mammalian diseases associated with undesired and uncontrolled angiogenesis, the method comprising administering to a mammal an anti-angiogenic compound of Formula I in an amount, i.e., a dosage, sufficient to inhibit angiogenesis. The particular dosage of a compound of Formula I required to inhibit angiogenesis and/or angiogenic diseases will depend upon the severity of the condition, the route of administration, and related factors that will be decided by the attending physician. Generally, accepted and effective daily doses will be the amount sufficient to effectively inhibit angiogenesis and/or angiogenic diseases.

The methods of treatment provided by this invention are practiced by administering to a mammal in need thereof a dose of a compound of Formula I (or a pharmaceutically acceptable salt or solvate thereof) that is effective to inhibit angiogenesis and/or angiogenic diseases. The term "inhibit" is used herein to include its generally accepted meaning which includes prophylactically treating a human subject to incurring angiogenesis and/or angiogenic diseases, and holding in check and/or treating existing angiogenesis and/or angiogenic diseases. As such, the present invention includes both medical therapeutic and/or prophylactic treatment, as appropriate.

The methods of the present invention can be used to treat a wide variety of diseases. Diseases associated with corneal neovascularization that can be treated using the methods of the present invention include, but are not limited to, diabetic retinopathy, retinopathy of prematurity, corneal graft rejection, neovascular glaucoma and retrolental fibroplasia, epidemic keratoconjunctivitis, vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, rheumatoid arthritis, systemic lupus, polyarteritis, Wegeners sarcoidosis, Scleritis, Stevens-Johnson disease, periphigoid radial keratotomy, and corneal graph rejection.

Diseases associated with retinal/choroidal neovascularization that can be treated using the methods of the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue, including all forms of proliferative vitreoretinopathy, whether or not associated with diabetes.

Diseases associated with chronic inflammation can also be treated using the methods of the present invention. Diseases with symptoms of chronic inflammation include, but are not limited to, inflammatory bowel diseases, such as Crohn's disease and ulcerative colitis, psoriasis, sarcoidosis and rheumatoid arthritis. Unwanted or uncontrolled angiogenesis is a key element that these chronic inflammatory diseases all have in common. The chronic inflammation depends on continuous formation of capillary sprouts to maintain an influx of inflammatory cells. The influx and presence of the inflammatory cells produce granulomas and, thus, maintain the chronic inflammatory state. Inhibition of angiogenesis using the compositions and methods of the present invention prevents the formation of the granulomas, thereby alleviating the disease.

As mentioned above, the methods of the present invention can be used to treat patients with inflammatory bowel diseases, such as Crohn's disease and ulcerative colitis. Crohn's disease occurs as a chronic transmural inflammatory disease that most commonly affects the distal ileum and colon, but may also occur in any part of the gastrointestinal tract from the mouth to the anus and perianal area. Patients with Crohin's disease generally have chronic diarrhea associated with abdominal pain, fever, anorexia, weight loss and abdominal swelling. Prevention of angiogenesis by the compositions and methods of the present invention inhibits the formation of the sprouts and prevents the formation of granulomas. Ulcerative colitis is also a chronic, nonspecific, inflammatory and ulcerative disease arising in the colonic mucosa and is characterized by the presence of bloody diarrhea.

The inflammatory bowel diseases also exhibit extra intestinal manifestations, such as skin lesions. Such lesions are characterized by inflammation and angiogenesis and can occur at many sites other than in the gastrointestinal tract. The compositions and methods of the present invention can also be used to treat these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease can form anywhere in the body and, thus, the symptoms depend on the site of the granulomas and whether the disease active. The granulomas are created by the angiogenic capillary sprouts providing a constant supply of inflammatory cells. The compounds and method of this invention can be used to treat sarcoidosis.

The methods of the present invention can also be used to treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease, which can be treated using the methods of the present invention, is rheumatoid arthritis. Rheumatoid arthritis is a chronic inflammatory disease characterized by nonspecific inflammation of the peripheral joints. It is thought that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated using the methods of the present invention are hemangiomas, Osler-Weber-Rendu disease, or hereditary hemorrhagic telangiectasia, solid or blood borne tumors and acquired immune deficiency syndrome.

The methods of this invention are also effective in inhibiting angiogenesis associated with malignant tumor growth. This includes cancerous tumor growth on cells tissues and organs. The methods of the present invention are useful in treating the growth of a number of tumor cells and for treating a wide variety of cancers. Such tumor cells include, by way of example and not limitation, lung, colon, breast, ovarian, prostate and hepatic tumor cells as well as squamous cell carcinomas. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas.

In a particularly preferred embodiment, the present invention relates to methods of administering compounds of Formula I in combination with active immunotherapy (e.g., tumor vaccination). Because the compounds of Formula I are not immunotoxic, the immune system is not significantly suppressed and, thus, active immunotherapy can advantageously be carried out in combination with the chemotherapy. When used in conjunction with immunotherapy, the compound of Formula I can be administered prior to and/or during administration of the immunotherapeutic agent (e.g., a tumor vaccine).

In still another embodiment, the present invention provides a method for reducing the level of TNF-α produced by a cell. TNF-α and its various modes of action are generally described by Abbas, et al., *Cellular and Molecular Immunology*, Abbas, et al., 2nd Ed., W. B. Saunders Company, 1994, pp. 244–249, the teachings of which are incorporated herein by reference. TNF-α plays an integral role in destroying tumors, mediating responses to tissue injury and protecting hosts from infections by various microorganisms. However, its activity appears to be excessive in some disease states and inflammatory reactions such as rheumatoid arthritis, cachexia and septic shock. The excess TNF-α results in an exaggerated immune response exemplified by over stimulation of interleukin-6 and granulocyte/macrophage-colony stimulating factor (GM-CSF) secretion, enhanced cytotoxicity of polymorphonuclear neutrophils and prolonged expression of cellular adhesion molecules, all of which can have detrimental effects.

Contacting cells with the compounds of Formula I results in decreased levels of TNF-α. Reduced levels of TNF-α can result from any of several mechanisms including, for example, downregulation of expression of a gene that encodes TNF-α, a reduction in TNF-α mRNA stability or translation efficiency, decreased stability of the TNF-α polypeptide, and reduced secretion of TNF-α from a cell. Reduced levels of TNF-α can be measured in a cell, biological sample or the blood stream. As a result of their ability to inhibit TNF-α, the compounds of Formula I can be used to treat inflammatory diseases. Such diseases include, but are not limited to, the inflammatory diseases set forth above (e.g., chronic inflammation, chronic disease, inflammatory bowel disease, sarcoidosis, psoriasis, rheumatoid arthritis, and the like). Using the assay set forth in Example VIII, compounds of Formula I can readily be screened for their ability to reduce TNF-α levels.

TNF-α is noted for its pro-inflammatory actions which result in tissue injury, such as induction of procoagulant activity on vascular endothelial cells, increased adherence of neutrophils and lymphocytes, and stimulation of the release of platelet activating factor from macrophages, neutrophils and vascular endothelial cells. As such, targeting moieties, which are directed to these cells and which are conjugated to liposomes or other drug delivery systems comprising the compounds of Formula I are preferred embodiments of this invention. For instance, in a preferred embodiment, monoclonal antibodies to TNF-α (Tracey, et al., *Nature* 1987, 330, 662–664; Silva, et al., *J. Infect. Sis.* 1990, 162, 421–427; and Williams, et al., *Proc. Natl. Acad. Sci.* 1992, 89, 9784–9788) are conjugated to liposomes comprising compounds of Formula I.

Moreover, in accordance with the above methods, mammalian subjects include, but are not limited to, humans, laboratory animals, domestic pets and farm animals.

D. PHARMACEUTICAL FORMULATIONS/ROUTES OF ADMINISTRATION

In the methods of the present invention, the compounds of Formula I can be delivered or administered to a mammal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to depress, suppress or inhibit angiogenesis or result in amelioration of symptoms associated with angiogenic diseases.

The compounds of Formula I, which are used in the methods of the present invention, can be incorporated into a variety of formulations for therapeutic administration. More particularly, compounds of Formula I can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

In addition, the compounds of Formula I can be formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

Compounds of Formula I can be administered alone, in combination with each other, or they can be used in combination with other known compounds (e.g., other anti-cancer drugs or other drugs, such as AZT, anti-inflammatories, antibiotics, corticosteroids, vitamins, etc.). For instance, the compound of Formula I can be used in conjunctive therapy with other known anti-angiogenic chemotherapeutic or antineoplastic agents (e.g., vinca alkaloids, antibiotics, antimetabolites, platinum coordination complexes, etc.). For instance, the compounds of Formula I can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known anti-angiogenic chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

Suitable formulations for use in the present invention are found in *Remington's Pharmaceutical* Sciences (Mack Publishing Company, Philadelphia, Pa., 17th ed. (1985)), which is incorporated herein by reference. Moreover, for a brief review of methods for drug delivery, see, Langer, *Science* 249:1527–1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula I can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. In a presently preferred embodiment, long-circulating, i.e., stealth, liposomes are employed. Such liposomes are generally described in Woodle, et al., U.S. Pat. No. 5,013,556, the teaching of which is hereby incorporated by reference.

Monoclonal antibodies optionally conjugated to liposomes and directed against a tumor marker, TNF-α, or a TNF-α receptor, is another strategy that can be employed. In addition, targeting of a marker on abnormal tumor vasculature can be employed. The targeting moiety when coupled to a toxic drug or radioisotope will act to concentrate the drug where it is needed. Ligands for tumor-associated vessel markers can also be used. For example, a cell adhesion molecule that binds to a tumor vascular element surface marker can be employed. Liposomes and other drug delivery systems can also be used, especially if their surface contains a ligand to direct the carrier preferentially to the tumor vasculature. Liposomes offer the added advantage of shielding the drug from most normal tissues, thereby reducing the inherent toxicity of many compounds. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity, and increased efficacy over non-targeted drug. Other targeting strategies include, but are not limited to, ADEPT (antibody-directed enzyme prodrug therapy), GDEPT (gene-directed EPT) and VDEPT (virus-directed EPT). In ADEPT, the targeting of an inactive prodrug to a tumor mass is effected by an antibody against a tumor-associated marker. The enzyme milieu in or about the tumor transforms the prodrug into an active toxic agent that then acts on the tumor tissue. Similarly, differential gene expression or viral targeting at the tumor site is used to activate a prodrug into its active, toxic form in GDEPT and VDEPT, respectively. Other strategies include targeting differentially expressed genes, enzymes or surface markers that appear on tumor-associated vasculature, to effect control of tumor growth. Using the foregoing methods, the compounds of Formula I can be targeted to the tumor vasculature to effect control of tumor progression or to other sites of interest (e.g., endothelial cells).

Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vivo data.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

F. EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example I

This example illustrates the synthesis of methyl-3,5-diiodo-4-(4-methoxyphenoxy)benzoate (BTO-956).

The synthesis of BTO-956 is accomplished in a series of steps, first yielding methyl 3,5-dinitro-4-(4-methoxyphenoxy)benzoate, the nitro groups of which are then reduced to amines and subsequently replaced by iodine. The method for preparing BTO-956 is essentially as described in: Masuda, K., Imashiro, Y., and Okada, Y. Synthesis of triiodothyroformic acid and its derivatives. J. Takeda Res. Lab. 1970, 29, 545–552.

1. Methyl 3.5-dinitro-4-(4-methoxyphenoxy)benzoate

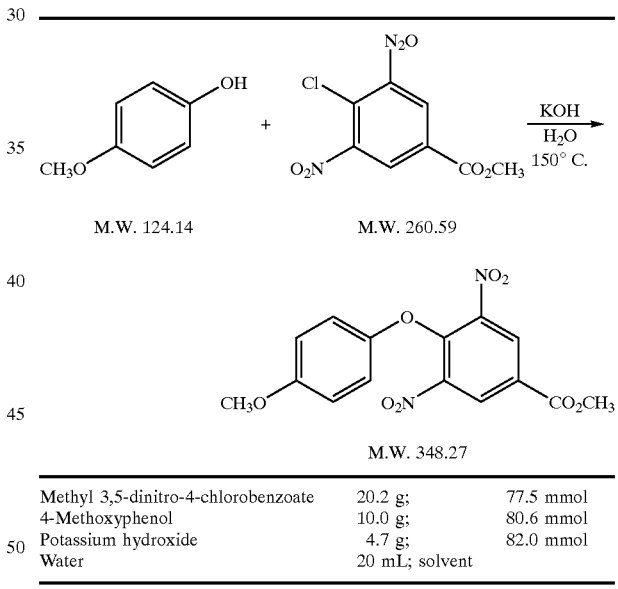

| | | |
|---|---|---|
| Methyl 3,5-dinitro-4-chlorobenzoate | 20.2 g; | 77.5 mmol |
| 4-Methoxyphenol | 10.0 g; | 80.6 mmol |
| Potassium hydroxide | 4.7 g; | 82.0 mmol |
| Water | 20 mL; solvent | |

To a 100 mL round-bottomed flask containing potassium hydroxide (4.7 g; 82.0 mmol) dissolved in water (20 mL) was successively added 4-methoxyphenol (10.0 g; 80.6 mmol) and methyl 4-chloro-3,5-dinitrobenzoate (20.2 g; 77.5 mmol). The flask was fitted with a reflux condenser and the reaction heated at 150° C. (oil bath) for 3 hours. After cooling to room temp, the reaction mixture was transferred to a large mortar and triturated with cold 2N NaOH (100 mL) to remove unreacted phenol. The solid was collected by filtration and air-dried to give 21.5 g of crude product. Crystallization from absolute ethanol gave 17.7 g (65.6%) of pure methyl 3,5-dinitro-4-(4-methoxyphenoxy)benzoate as light yellow needles. 300 MHz $^1$H NMR (CDCl$_3$) d 3.77 (s, 3H, OCH$_3$), 4.02 (s, 3H, OCH$_3$), 6.82 (m, 4H, ArH), 8.70 (s, 2H, ArH).

2. Methyl 3.5-diamino-4-(4-methoxyphenoxy)benzoate

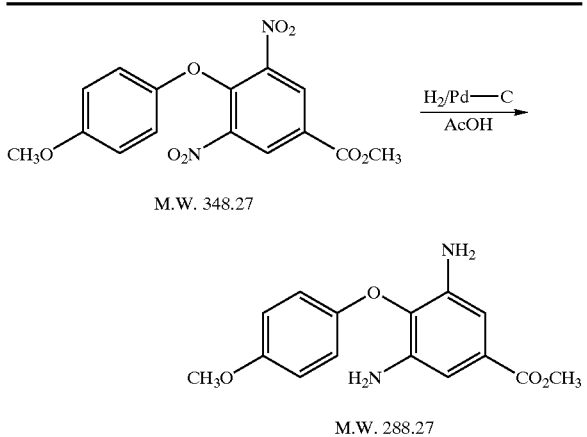

| Methyl 3,5-dinitro-4-(4-methoxyphenoxy)benzoate | 20.2 g; | 77.5 mmol |
|---|---|---|
| 10% palladium on charcoal | 0.7 g; | catalyst |
| Glacial acetic acid | 80 mL; | solvent |

To a Parr shaker bottle containing a suspension of methyl 3,5-di-nitro-4-(4-methoxyphenoxy)-benzoate (20.2 g; 77.5 mmol) in glacial acetic acid (80 mL) was added 10% palladium on charcoal (0.7 g). The bottle was shaken under an atmosphere of hydrogen (3 atm) until no more hydrogen was consumed. The catalyst was filtered off and the resulting solution concentrated to approximately 10 mL. The residue was dissolved in acetone (50 mL) and heated on a steam bath while water (100 mL) was added in portions. Upon cooling, medium brown needles formed which were collected by suction filtration and dried to give 7.1 g (86%) of methyl 3,5-diamino-4-(4-methoxyphenoxy)benzoate. 300 MHz $^1$H NMR (CDCl$_3$) d 3.73 (s, 3H, OCH$_3$), 3.80 (bs, 4H, ArNH$_2$) 3.86 (s, 3H, OCH$_3$), 6.84 (m, 4H, ArH), 6.91 (s, 2H, ArH).

3. Methyl-3.5-diiodo-4-(4-methoxyphenoxybenzoate

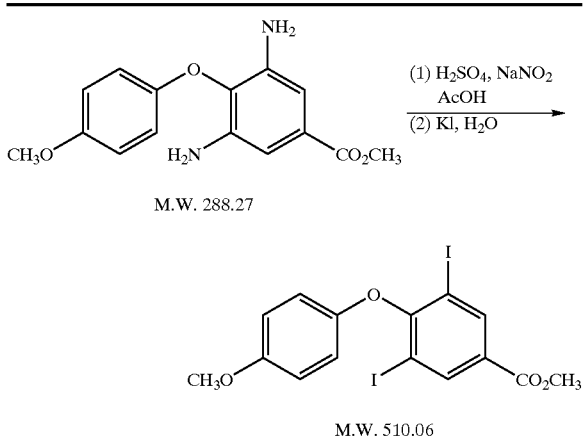

| Methyl 3,5-diamino-4-(4-methoxyphenoxy)benzoate | 4.3 g; | 14.2 mmol |
|---|---|---|
| Sodium nitrite | 2.6 g; | 37.4 mmol |
| Glacial acetic acid | 80 mL; | solvent |
| Sulfuric acid | 26 mL; | solvent |
| Potassium iodide | 20 g; | 120.0 mmol |
| Water | 30 mL; | solvent |

Sulfuric acid (26 mL) was placed in a three-necked flask equipped with a mechanical stirrer and cooled in an ice bath. Sodium nitrite (2.58 g, 37.4 mmol) was added in small portions, and the mixture was stirred for 20 min to form a thick solution. To this was added a slurry of methyl 3,5-diamino-4-(4-methoxyphenoxy)benzoate (4.30 g, 14.22 mmol) in glacial acetic acid (80 mL), dropwise over a period of 30 min, keeping the temperature below 10° C. with the ice bath. The reddish brown solution was stirred at below 10° C. for 45 min, after which it was poured slowly into an aqueous (30 mL) solution of potassium iodide (20 g) at room temperature, with vigorous stirring. A thick suspension formed, and was allowed to stir at RT for 1 h. The reaction mixture was then heated in an oil-bath to 80° C. (internal temperature) for 15 min, and then allowed to cool to RT. The solution was filtered and the black gummy residue was dissolved in 300 mL of acetone. The dark filtrate, when refrigerated overnight, deposited a dark residue, which was collected by decanting the supernatant, and the residue was dissolved in 100 mL of acetone. The combined acetone solution was filtered over a pad of basic alumina (5 cm) in a 150 mL sintered glass funnel to remove some colored impurities. The alumina pad was washed with 100 mL acetone and the red filtrate was evaporated to dryness, to give a dark solid as crude product. This was purified by flash chromatography on silica gel, eluting with hexanes: CH$_2$Cl$_2$ (60:40). Initial fractions containing the pure product were pooled and evaporated to yield 1.67 g of the desired product as an off-white solid. This compound gave a single, clean spot on TLC (Hexanes: CH$_2$Cl$_2$; 1:1; R$_f$ 0.35). Impure fractions were pooled and triturated with absolute EtOH for 16 hours at room temperature. The solid was filtered and dried to yield another 0.3 g of the product as a cream solid, which contained ~5% of the slow-moving impurity as evidenced by TLC (R$_f$ 0.29). Total yield of the product was 27%. 300 MHz $^1$H NMR (CDCl$_3$) d 3.78 (s, 3H, OCH$_3$), 3.94 (s, 3H, COOCH$_3$), 6.70 and 6.83 (two d, AA'XX', 4H, p-subs. Ar—H), 8.51 (s, 2H, Ar—H).

Example II

This example illustrates the anti-angiogenic properties of methyl-3,5-diiodo-4-(4'-methoxyphenoxy)benzoate in the chick chorioallantoic membrane assay (CAM). The endpoint of the CAM assay was a quantitative determination of basement membrane biosynthesis by measuring the incorporation of $^{14}$C-proline into Type IV collagenous protein.

A. Approach

The CAM assay involves the development of live chick embryos in Petri dishes under special sterile conditions. Therefore, only limited numbers of embryos can be used for evaluation of compounds in a single experiment. For this reason, two separate assays were conducted to test the three Biosource compounds at three concentrations per compound. In this assay, a known angiogenesis inhibitor, 2-methoxyestradiol (2-ME), was used as the positive control, and human fibroblast growth factor (hFGF) was used to induce angiogenesis in the CAM.

B. Materials

Fertilized eggs were supplied by Melody Ranch, Aptos, Calif. L-[U-$^{14}$C] proline (specific activity, 290 mCi/mmol) was purchased from New England Nuclear, Boston, Mass. Collagenase and 2-ME were obtained from Sigma Chemical Co., St. Louis, Mo. Silicone ring cups were obtained by cutting silicone tubing (3 mm diameter) into small "O" rings 1 mm in thickness. These silicone ring cups can be reused many times if they are sterilized prior to each assay. Plastic Petri dishes (20×100 mm) were purchased from Baxter Diagnostics, Inc., Hayward, Calif. hFGF-B was obtained from Clonetics Corporation, San Diego, Calif.

For testing, a minimum amount of acetone-methanol (1:1) was added to the test compounds for sterilization. The acetone-methanol mixture was then evaporated to dryness in a sterile hood. The compounds were dissolved dimethyl sulfoxide (DMSO) first and then diluted with saline containing methylcellulose. The final concentrations were 2% DMSO and 0.5% methylcellulose. All test solutions were added to each CAM in 20-mL aliquots.

C. Development of the CAM for Measuring Angiogenesis Inhibition

The method of Folkman, et al., *Dev. Biol.* 41: 391–394 (1974), with some modifications, was used to cultivate chicken embryos as follows:

Fresh fertile eggs were incubated for three days in a standard egg incubator. On Day 3, eggs were cracked under sterile conditions and embryos were placed in 20×100 mm plastic Petri dishes and cultivated at 37° C. in an embryo incubator with a water reservoir on the bottom shelf. Air was continuously bubbled into the water reservoir by using a small pump so that the humidity in the incubator was kept constant. Observations were made daily to ensure that all embryos were healthy. Dead or unhealthy embryos were removed from the incubator immediately to avoid contamination. On Day 9, a sterile silicone ring cup was placed on each CAM and 0.5 mCi of $^{14}C$-proline with or without the test compound plus 2.5 ng of hFGF dissolved in saline containing 0.5% methylcellulose was delivered into each ring cup in a sterile hood. 2-ME was tested in parallel to serve as a reference compound. After addition of test materials, the embryos were returned to the incubator and cultivation continued. On Day 12, all embryos were transferred to a cold room at 4–10° C. The antiangiogenic effect of each test compound was determined by using the collagenase assay (Maragoudakis, et al., *J. Pharm. Exp. Ther.* 251:679–682 (1989)) to measure $^{14}C$-proline incorporation into collagenous protein.

D. Collagenase Assay for Measurement of $^{14}C$-Proline Incorporation into Collagenous Protein With the embryos placed on ice, a piece of CAM 10 mm in diameter was cut off under each ring cup and placed in a separate tube. To each tube was added 1.0 mL of phosphate-buffered saline (PBS, pH 7.3) containing 0.11 mg cyclohex-imide and 0.17 mg dipyridyl. The tubes were placed in a boiling water bath for 10 min and then cooled to room temperature. The PBS in each tube was discarded after centrifugation at 3000× g for 10 min. The CAM residue was washed once with 3 mL of 15% TCA and then three times with 3 mL of 5% TCA. Centrifugation was carried out as described above between each washing. At this point all non-protein bound radioactivity was removed, and the CAM containing the newly synthesized $^{14}C$-collagenous protein was suspended in 0.9 mL of 0.1 N NaOH and 1.1 mL of HEPES buffer at pH 7.4. The pH of the sample was neutralized with 0.8 N HCl, using phenol red as indicator.

To digest the $^{14}C$-collagenous protein, 7.5 units of collagenase and 500 nmol of calcium chloride in 40 mL of HEPES buffer was added to the above samples, and mixtures were incubated at 37° C. for 4 h. The reaction was stopped by adding 1.0 mL of 20% TCA containing 5 mg of tannic acid into each tube. After vortex mixing, the samples were centrifuged at 3000× g for 10 min. An aliquot of the clear supernatant was taken for scintillation counting to quantitate the radiolabeled tripeptides corresponding to basement membrane collagen and other collagenous materials synthesized by the CAM from $^{14}C$-proline. The CAM pellets in each tube were solubilized in 0.5 mL of 1.0 N NaOH by boiling in a water bath for 5 min. An aliquot of the dissolved CAM was used for protein determination using the method provided by Pierce Chemical Co. (Instruction manual for protein assay using bicinchoninic acid (BCA) Pierce Chemical Co., Rockford, Ill.). The radioactivity per milligram of protein from the CAM treated with a test compound relative to that from the control CAM gave the percent of angiogenesis inhibition.

E. Results

Tables 1 and 2 summarize the results of the two separate experiments. BTO-956 showed statistically significant inhibitory effects on hFGF-B-induced angiogenesis. At 75 mg/CAM, the inhibition caused by BTO-956 was 30%, compared to 38% caused by the same concentration of the known antiangiogenic agent, 2-methoxyestradiol. The results from these two experiments suggest that the antiangiogenic effect of BTO-956 in the CAM assay is on the same order as that of 2-methoxyestradiol, a drug that is under development as an antiangiogenic agent.

TABLE 1

INHIBITORY EFFECTS OF COMPOUNDS ON ANGIOGENESIS INDUCED BY hFGF-B

| Compound | Dose ($\mu$g/CAM) | $^{14}C$-Proline Incorporated into Collagenous Protein (cpm/mg-protien) (mean ± S.E.) | % IN-HIBITION |
|---|---|---|---|
| BTO-956 | 75 | 4374 ± 651 | 31 |
|  | 25 | 5098 ± 785 | 19 |
|  | 8.3 | 6884 ± 1395 | 0 |
| 2-Methoxyestradiol | 75 | 3875 ± 891 | 38 |
|  | 25 | 5068 ± 1609 | 20 |
|  | 8.3 | 5711 ± 1469 | 9 |
| Control | — | 6300 ± 696 | — |

TABLE 2

INHIBITORY EFFECTS OF COMPOUNDS ON ANGIOGENESIS INDUCED BY hFGF-B

| Compound | Dose ($\mu$g/CAM) | $^{14}C$-Proline Incorporated into Collagenous Protein (cpm/mg-protien) (mean ± S.E.) | % Inhibition |
|---|---|---|---|
| BTO-956 | 75 | 7534 ± 1099[a] | 32 |
|  | 25 | 9100 ± 1664 | 18 |
|  | 8.3 | 10138 ± 1625 | 10 |
| 2-Methoxyestradiol | 75 | 6984 ± 1022[b] | 38 |
|  | 25 | 7303 ± 1424 | 35 |
|  | 8.3 | 10499 ± 1372 | 6 |
| Control | — | 11200 ± 829 | — |

[a]Significantly lower than control, P < 0.02.
[b]Significantly lower than control, P < 0.01.

Example III

This example illustrates the determination $ID_{50}$ of BTO-956 on the proliferation of human microvascular endothelial cells (HMVEC).

Human microvascular endothelial cells (HMVEC) (Clonetics Corporation, #CC-2505) were seeded into 96-well plates at a concentration of $5 \times 10^3$ cells/well in a volume of 100 $\mu$l/well of Endothelial Growth Medium (EGM-2-MV, Clonetics Corporation #CC-3162). Plates were incubated at 37° C. in 5% $CO_2$ for 24 h and then covered with 100 $\mu$/well of EGM-2-WV. BTO-956 was diluted to 20 mM in dimethyl sulfoxide (DMSO) and further diluted with EGM-2-MV to 2× the concentrations reported below. Then 100 $\mu$l aliquots of BTO-956/EGM-2-MV dilutions were added to the HMVEC preparations and plates were incubated at 37° C. in 5% $CO_2$ for 3 days. The relative number of cells was determined by adding 20 $\mu$l/mL of Alamar Blue (BioSource International #DAL-1025) for 3–6 h at 37° C. and measuring color changes indicating metabolic activity by using a Millipore Cytofluor 2350 Fluorescence Measurement System at an excitation wavelength of 530 nm and an emission wavelength of 590 nm. In this assay, the intensity of the fluorophore signal is directly proportional to cell number.

A broad range curve was first established for BTO-956 to determine the concentrations to use for a narrow range curve. A narrow range curve was then generated to find a region around the $ID_{50}$ point at which the curve is linear. The $ID_{50}$ was calculated by using the linear portion of the curve in the immediate area around the dose giving 50% inhibition and using the equation y=ax+b, where x is the calculated $ID_{50}$, y is 50% of the maximum optical density (OD), and a and b are constants.

To establish an exact $ID_{50}$ for BTO-956, a narrow concentration range was tested on HMVECs (from 450 nM to 50 nM). Maximum inhibition was determined by using an additional upper concentration limit of 10 μM. The baseline value was determined by using medium without compound. The $ID_{50}$ was determined to be 201 nM on Day 3.

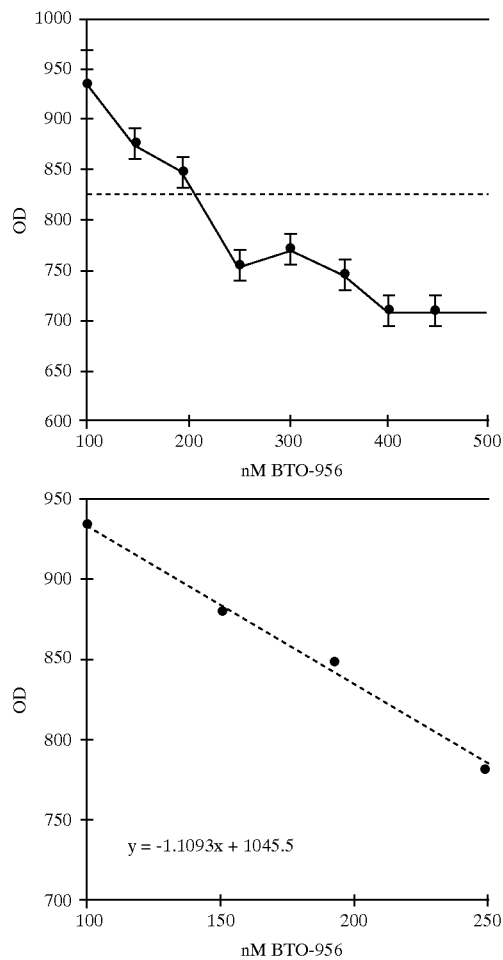

Example IV

A. BTO-956 is Orally Bioavailable and has Minimal Normal Tissue Toxicity

Gavage administration of BTO-956 to nude mice at doses as high as 1,000 mg/kg-day for 60 to 180 days produced only slight and transient increases in liver and kidney weights. No other gross pathology was observed. No mortality was seen at a daily administration of 4,000 mg/kg-day of BTO-956 for 3 weeks. Because a common toxic effect of anti-proliferative chemotherapeutic agents is myelosuppression caused by depletion of bone marrow stem cells, we tested the possibility that BTO-956 may have bone marrow toxicity. Swiss Webster mice were exposed to the drug at 500 mg/kg-day by gavage for a period of 4 weeks, and bone marrow was examined histologically. The bone marrow profiles of treated animals did not differ from those of control animals exposed only to the carrier vehicle, and no hematopoietic abnormalities were found. Both myeloid and erythroid lineages were observed at various stages of maturation. These results demonstrate that oral administration of BTO-956 is well tolerated by animals exposed to the drug for periods of up to six months, and has no obvious myelosuppressive activity after one month of daily administration at a therapeutic dose. Preliminary studies (not shown) indicate that therapeutic oral doses of BTO-956 are within the range of 500 to 1,000 mg/kg-day.

Figure 1B:
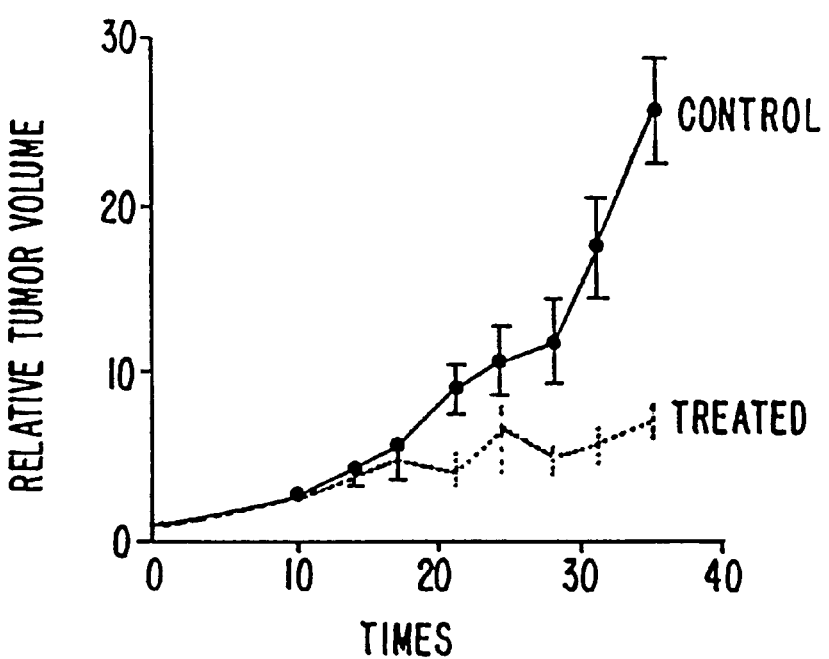

B. BTO-956 Has Strong Growth Delay Effects in Human Breast and Ovarian Carcinoma Xenografts Swiss NCr nude (nu/nu) female mice implanted with MDA MB-231 human breast carcinoma xenografts showed a strong growth delay response to oral treatment with BTO-956 (FIG. 1). Intraperitoneally administered cyclophosphamide (CTX; Cytoxan; 150 mg/kg), which is used in some regimens for adjuvant breast cancer therapy was used as a positive control. Growth of tumors in the BTO-956-treated group was suppressed during 6 weeks of therapy while those in the control vehicle-treated animals increased approximately 5-fold on the average (relative mean tumor volume; FIG. 1A). BTO-956 was also effective in inhibiting the growth of OVCAR-3 human ovarian carcinoma xenografts (FIG. 1B). Using the same schedules and doses as those described for the MDA MB-231 breast tumor study, but with shorter study duration, the relative mean tumor volume at 5 weeks of animals exposed to BTO-956 was again approximately 5-fold less than that of the vehicle-treated controls. Two important conclusions of this study are the following: (1) BTO-956 is effective as a cytostatic/cytotoxic antitumor drug when administered orally; and (2) BTO-956 is essentially nontoxic even at very high orally administered doses.

C. BTO-956 Induces a Mitotic Arrest in MCF-7 Human Breast Carcinoma Cells

Figures 2A, 2B, 2C:
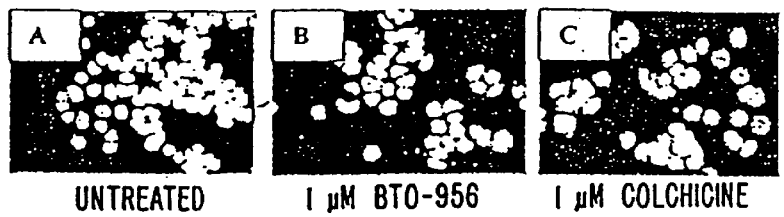
FIGS. 2(A)–(C) illustrates that BTO-956 induces a prometaphase arrest in MCF-7 breast carcinoma cells.

Having demonstrated significant antitumor effects of BTO-956 in vivo, we investigated its cytotoxicity toward human breast carcinoma cells in vitro. The $IC_{50}$ (concentration for 50% reduction of cell number relative to that of a vehicle-treated control) of BTO-956 in MDA MB-231 and MCF-7 cell cultures treated for 48 h was 0.3 μM and 0.6 μM, respectively. Investigation of the effect of BTO-956 (1 μ for 48 h) on the nuclear morphology of these cells demonstrated that a significant number had condensed or fragmented nuclei characteristic of apoptotic cell death. To test whether BTO-956 exerts its cytotoxicity by perturbing the cell cycle, MCF-7 cultures were exposed to the drug at 1 μM for 24 h (FIG. 2). A large fraction of these cells showed chromosome condensation characteristic of a prometaphase arrest (FIG. 2B). In agreement with this conclusion, treatment of MCF-7 cells with the antimitotic drug colchicine (1 μM) for 24 h produced identical chromosome condensation patterns (FIG. 2C). After 48 h of exposure to 1 μM BTO-956, MCF-7 cells showed substantial cytotoxicity based on the criterion of loss of membrane integrity measured by a trypan blue exclusion assay. This result is consistent with that of the tumor growth delay study described above, and demonstrates that BTO-956-induced cell death occurs subsequent to a prometaphase arrest in human breast carcinoma cell cultures.

To investigate the mitotic arrest caused by BTO-956 in more detail, flow cytometry was used to determine the effect of the drug on the cell-cycle progression of MCF-7 cells. These experiments showed that at least 60% of these cells arrested at $G_2/M$ within 24 h of treatment with 1 $\mu$M BTO-956. The same finding was obtained for MDA MB-231 cells exposed to the drug under the same conditions. These results demonstrate that BTO-956 causes human breast carcinoma cells to accumulate at the $G_2/M$ cell-cycle interphase, presumably by activating a mitotic spindle-assembly checkpoint. Such arrested cells eventually undergo cell death which can occur by an apoptotic mechanism.

D. BTO-956 Inhibits Microtubule Dynamics Both In Vitro and in Cultured Cells

Figures 3A, 3B, 3C, 3D:
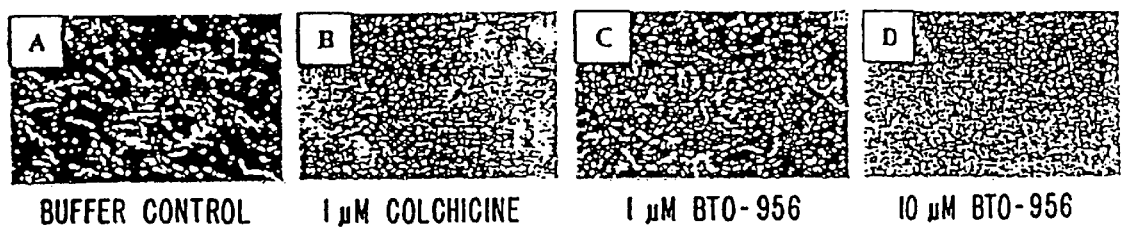
FIGS. 3(A)–(D) illustrates the inhibition of in vitro microtubules assembly by BTO-956.
Figure 4A:
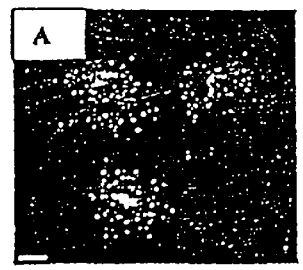
FIGS. 4(A)–(B) illustrates the disruption of microtubule networks by BTO-956.
Figure 4B:
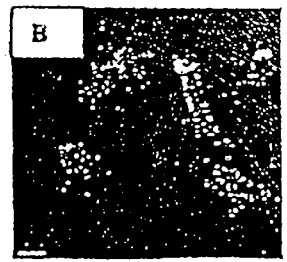

Microtubules are major cytoskeletal components composed of $\alpha$- and $\beta$-tubulin heterodimers bound with GTP. Antimitotic drugs such colchicine, Vinca alkaloids, and paclitaxel (Taxol) perturb the intrinsic dynamic instability of microtubules arising from GTP hydrolysis by binding directly to tubulin and causing inhibition of spindle formation with consequent mitotic arrest. To determine whether the antimitotic effect of BTO-956 exposure could be explained by tubulin-binding activity, two studies were performed. The effect of the drug on microtubule assembly was investigated directly by using a cell-free fluorescence assay involving the visualization of microtubule formation from rhodamine-labeled tubulin and microtubule seeds in the presence of GTP. In this assay, 15 $\mu$M tubulin rapidly polymerized to form long, bright microtubule threads in the absence of a tubulin-binding agent (FIG. 3A), whereas in the presence of 1 $\mu$M colchicine microtubule formation was completely inhibited (FIG. 3B). The same effect was observed in the presence of 10 $\mu$M BTO-956 (FIG. 3D). At a concentration of 1 $\mu$M BTO-956 was less potent, but nonetheless produced much shorter structures than those visible in the control experiment (FIG. 3C). In a second study, the ability of BTO-956 to perturb cellular microtubule assembly was investigated by using HeLa cells (FIG. 4), which also arrest at mitosis when exposed to the drug (FIG. 4) shows that HeLa cells exposed to 10 $\mu$M BTO-956 for 1 h had aberrant microtubule networks resembling those created by exposure to 1 $\mu$M colchicine. Taken together, these findings demonstrate that BTO-956 can interact directly with tubulin in vitro and in cells to inhibit microtubule formation, much like the antimitotic drug colchicine.

E. BTO-956 Competes with Colchicine for Binding to Tubulin In Vitro

Figure 5:
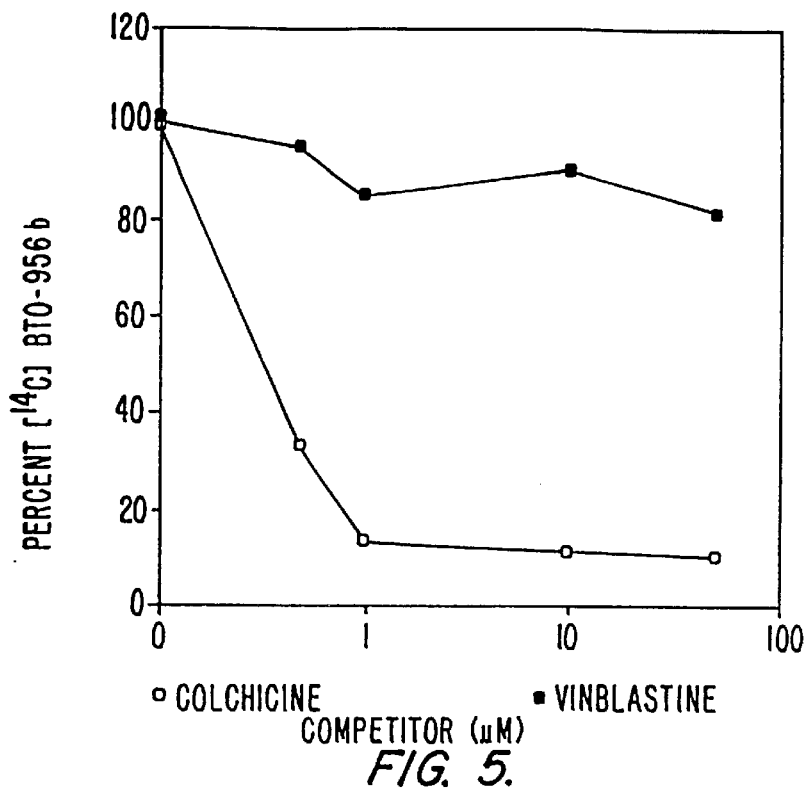
FIG. 5 illustrates that BTO-956 competes with colchicine for binding to tubulin in vitro.
Figure 6:
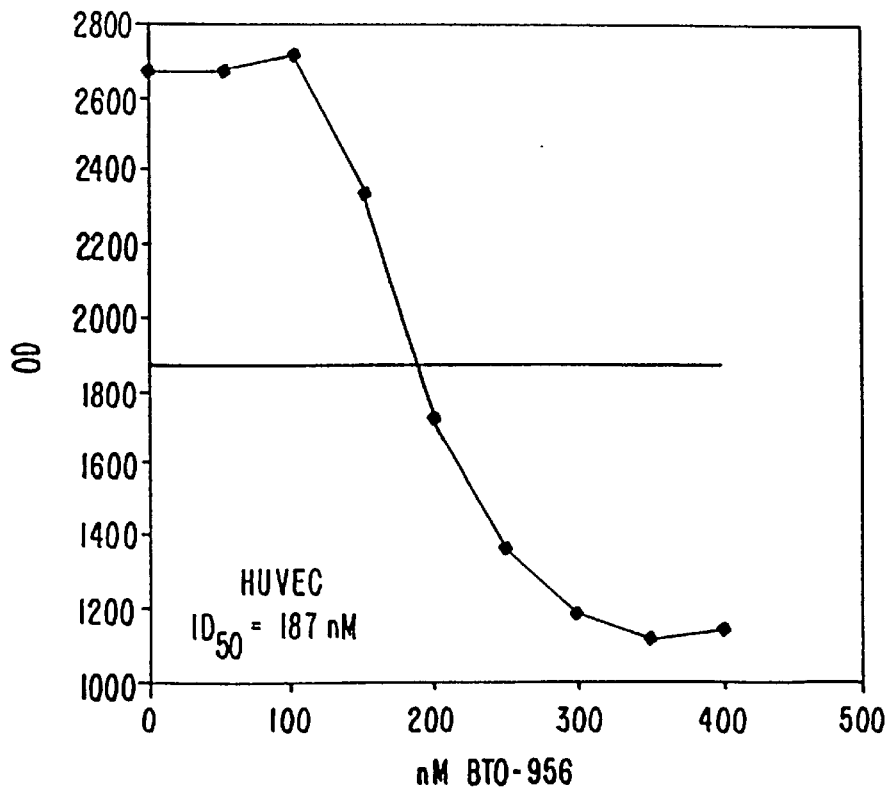
FIG. 6 illustrates that BTO-956 inhibits the proliferation of human vascular endothelial cells.
Figure 7:
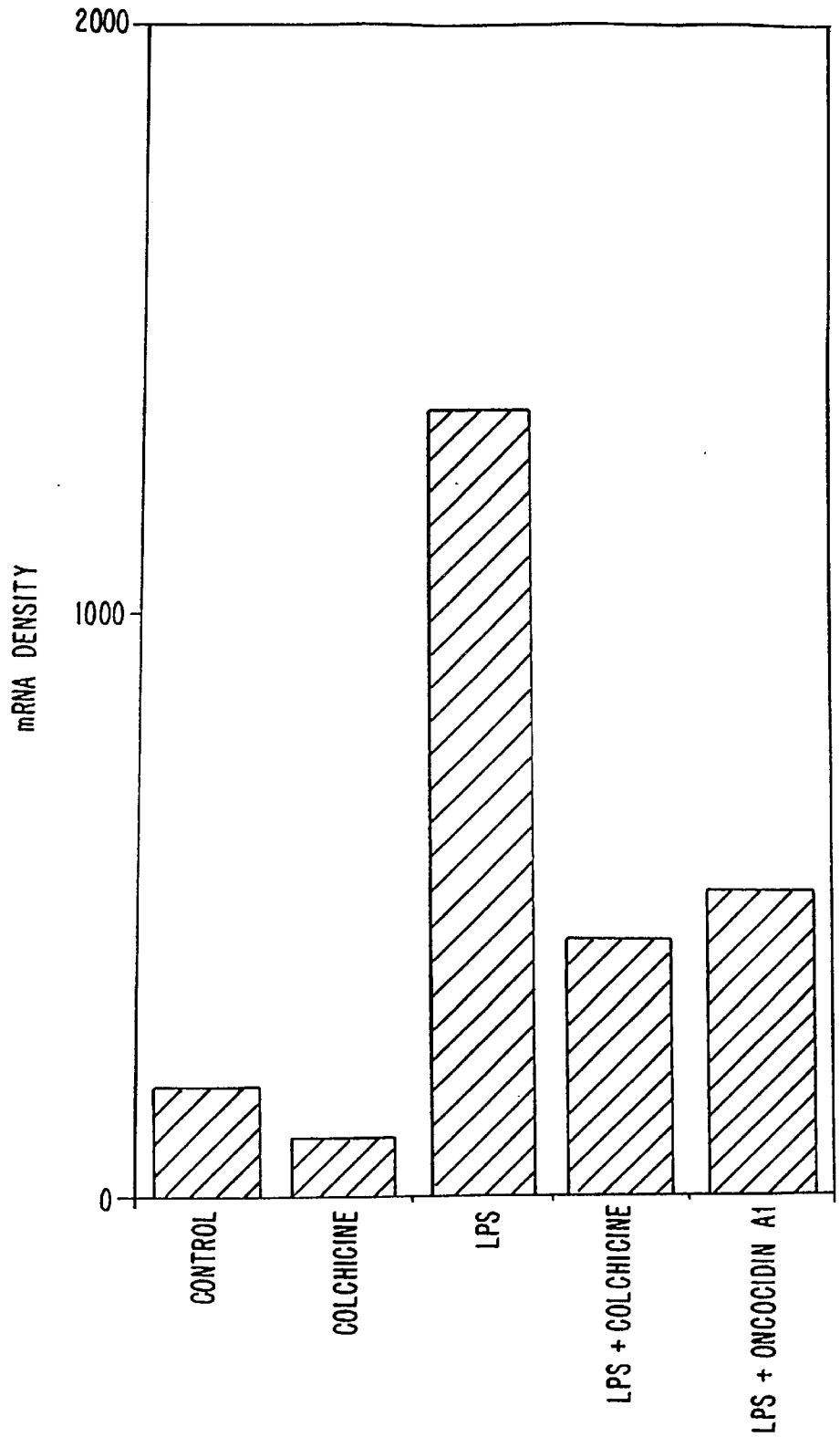
FIG. 7 illustrates that BTO-956 reduces TNF-α mRNA accumulation.
Figure 8:
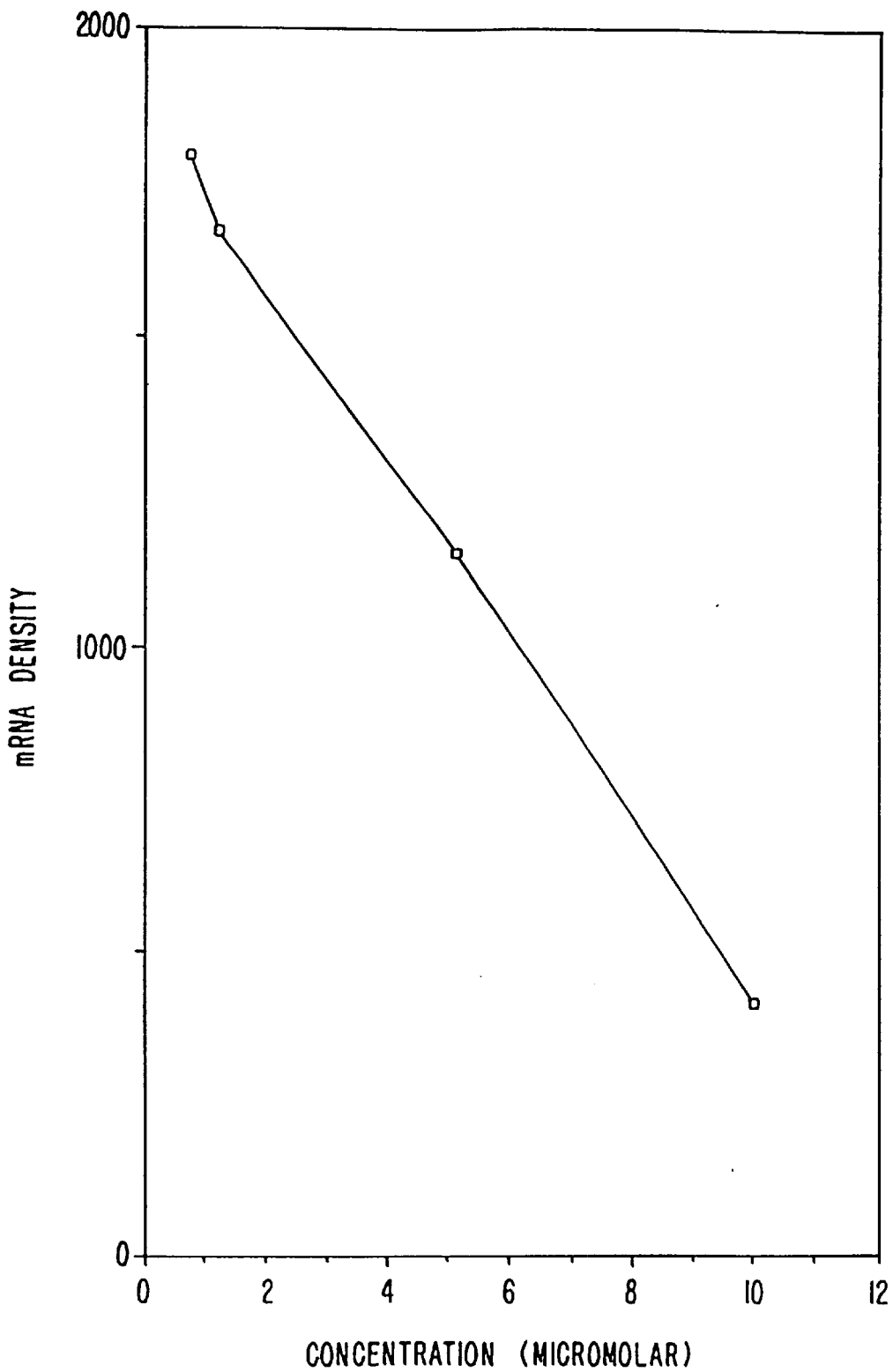
FIG. 8 illustrates the effect of different concentrations of BTO-956 on TNF-α gene expressions.
Figure 9:
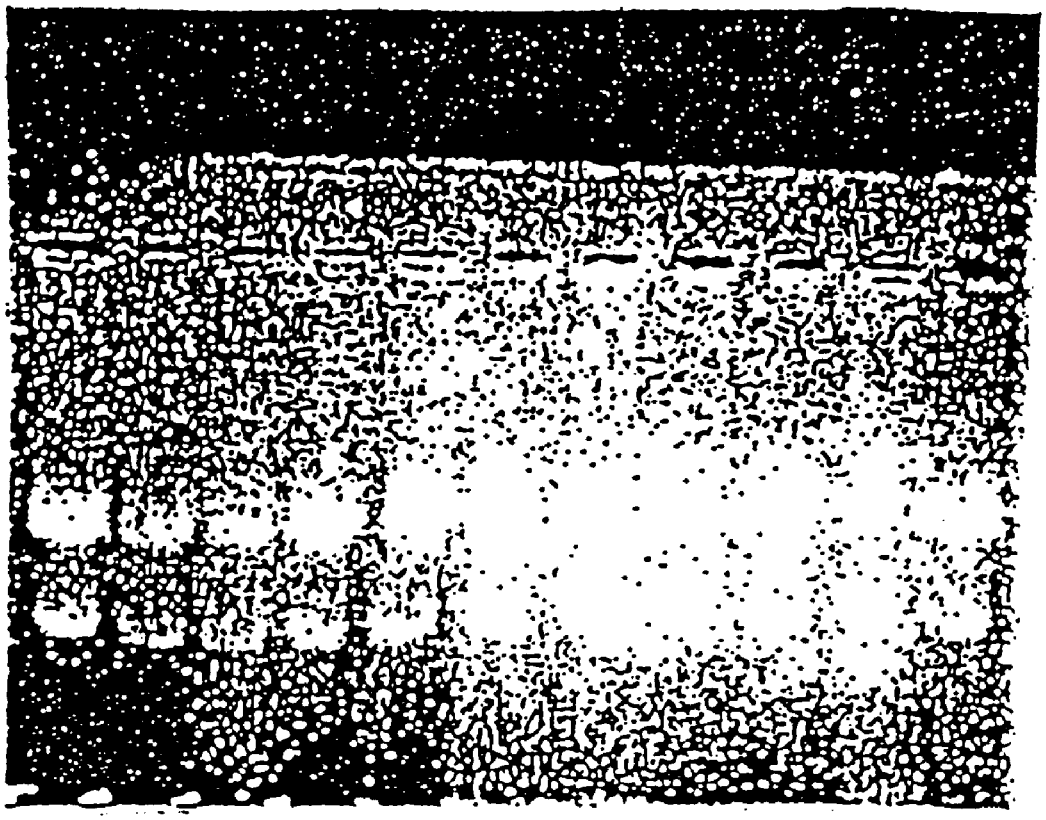
FIG. 9 illustrates that total RNA was intact in cells treated with different concentrations of BTO-956 and colchicine.

Tubulin-binding antimitotic drugs interact with the protein at diverse sites. Colchicine binds to soluble tubulin heterodimers at a single high-affinity site (the colchicine binding site) to form a kinetically inert complex. Vinblastine binds to one or two identical high-affinity sites on tubulin (Vinca alkaloid binding sites) that are different from the colchicine site. To determine whether the effect of BTO-956 on microtubule assembly is mediated by a specific site on tubulin, the ability of $^{14}$C-labeled drug to compete with colchicine or vinblastine for binding to purified tubulin was measured as a function of colchicine or vinblastine concentration. FIG. 5 demonstrates that colchicine inhibited the binding of BTO-956 to tubulin, whereas vinblastine had no effect. This finding indicates that BTO-956 interacts directly or indirectly with the colchicine site but not the Vinca alkaloid high-affinity binding sites of tubulin in vitro.

Example V

This example demonstrates that BTO-956 can downregulate the expression of cytokines in lipopolysaccharide-stimulated murine macrophages. The following is an assay for measuring the ability of Compounds of Formula I to reduce the levels of Tumor Necrosis Factor (TNF-$\alpha$).

A. Cell Line

The murine macrophage PU5–1.8 cell line was purchased from the American Type Culture Collection (ATCC, Rockville, Md.). Cells were grown in DMEM medium supplemented with 100 mM sodium pyruvate, 0.1 mM nonessential amino acids, 2 mM glutamine and 5% fetal bovine serum (Life Technologies, Staten Island, N.Y.). Cells were maintained in a humidified atmosphere of 5% $CO_2$-95% air at 37° C. Cells were passages twice weekly by firmly tapping the side of the flask to dislodge the adherent cells. Both nonadherent and adherent cells were passages. Exponentially growing cells were seeded at $5 \times 10^5$/mL, 4mL per 60-mm dish 24 h prior to the experiment. Test compounds were delivered in 1 mL volumes of the medium added to each dish at the start of the experiment. All dishes were incubated at 37° C. in 5% $CO_2$-95% air for 3 h.

B. Reagents

The Tumor Necrosis Factor (TNF-$\alpha$) cDNA was obtained from the ATCC (Rockville, Md.). [$\alpha$-$^{32}$P]-dCTP (250 $\mu$Ci) and nylon membranes (Hybond N) were obtained from Amersham (Arlington Heights, Ill.). Colchicine (used as a control) was purchased from the Sigma Chemical Company (St. Louis, Mo.). Lipopolysaccharide (LPS) from *Escherichia coli* was purchased from DIFCO Laboratories (Detroit, Mich.). All plastic supplies were from VWR Scientific products (San Francisco, Calif.).

C. Northern Blotting

Total RNA was isolated by the guanidinium-cesium chloride method as described in N. S. Waleh, J. Gallo, T. D. Grant, B. J. Murphy, R. H. Kramer and R. M. Sutherland. (1994) "Selective downregulation of integrin receptors in spheroids of squamous cell carcinoma" *Cancer Res.*, 54:838–843. Five to 10 $\mu$g of total RNA was electrophoresed in 1% agarose gels containing 6% formaldehyde. Following electrophoresis, gels were stained with ethidium bromide to visualize the positions of 28S and 18S RNA. The RNAs were then transferred to nylon membranes (Amersham Hybond N) by capillary blotting and fixed to the filter by exposure to UV light. The blots were probed with $^{32}$P-labeled cDNA sequences of human TNF-$\alpha$ obtained from the American Type Culture Collection (ATCC). The TNF-$\alpha$ cDNA was a 1.1 kb PstI fragment of plasmid pE4 in *E. coli* MM294 (ATCC 39894). Hybridizations were carried out at 42° C. in 50% formamide, 5×SSC, 5×Denhardt's solution, 0.1% SDS, and 0.3 mg/mL salmon sperm DNA. Filters were washed by 1×SSC, 0.1% SDS, twice at room temperature for 15 min and once at 55° C. in 0.1×SSC, 0.1% SDS for 1 hr. Filters were exposed to X-ray film at −70° C. using an intensifying screen (Coronex Hi-Plus).

Hybridized bands were quantified by analyzing the images obtained by using a video densitometer (Applied Imaging Corporation, Santa Clara, Calif.). Film densities were calibrated using an optical-density wedge.

D. RESULTS

Treatment of PU5–1.8 murine macrophages with LPS (100 ng/mL) for 3 h resulted in a significant increase (>7 fold) in the level of TNF-$\alpha$ mRNA as determined by Northern blot analysis (see, FIG. 1). Treatment of cells with only BTO-956 or colchicine at 10 $\mu$M concentration had no effect on TNF-$\alpha$ mRNA expression. However, addition of colchicine or BTO-956 at 10 $\mu$M to the LPS treated cultures resulted in substantial reduction of TNF-$\alpha$ mRNA accumulation. The inhibition levels were 68% for colchicine and 61% for BTO-956, respectively.

To establish a concentration-effect relationship, macrophages were exposed to various concentrations of BTO-956 in the presence of the stimulus LPS for 3 h. FIG. 2 illustrates that the amounts of TNF-α mRNA declined with the increasing concentrations of BTO-956. The maximum effect was observed at 10 μM concentration of BTO-956. Total RNA was intact in cells treated with different concentrations of BTO-956 and colchicine, suggesting toxicity was not problematic.

The results indicate that BTO-956 at 10 μM partially suppresses, but does not completely inhibit, the expression of TNF-α mRNA in the murine macrophage cell line PU5-1.8. This indicates that BTO-956 downregulates LPS-stimulated responses by affecting the microtubule-dependent signaling pathways.

This finding is of clinical interest because BTO-956 can be used as a new class of compounds to prevent LPS-mediated excessive TNF-α production and its undesired side effects. This is especially attractive because BTO-956 has been shown to be a safe and well tolerated drug when administered orally to animals.

Example VI

This example demonstrates that BTO-956 has strong antiproliferative activity toward human microvascular endothelial cells in vitro and substantial anti-angiogenic activity in vivo, as assessed by its effect on rat corneal neovascularization.

Materials and Methods

A. The Rat Corneal Neovascularization Assay.

Hydron polymer (Interferon Sciences, New Brunswick, N.J.) was dissolved in ethanol to a concentration of 12% (W/V). A 1:1 mixture of 12% Hydron and bFGF/Sucralfate/PBS suspension was made as a casting solution and 3 μl of this solution was pipetted onto a sterile Teflon sheet and allowed to dry overnight at 4° C. Each dried pellet contained 50 ng of bFGF and 20 μg of Sucralfate. Female Fischer 344 rats (16 animals, 8–10 weeks old at an approximate weight of 150 g; Charles River, Raleigh, N.C.) were used for this study. Animals were kept in temperature-controlled rooms (24° C.) on a 12-h light-dark cycle with access to rat chow and tap water ad libitum. Following anesthesia with sodium pentobarbital given i.p. at 50 mg/kg body weight, a rat was placed under a dissecting microscope and a drop of Ophthaine was applied on the cornea of one eye. The eye was proptosed by stretching sutures on the upper and lower eyelids. A small superficial incision was made through the cornea center and a micropocket was created by separating the lamella of the stroma toward the limbus with a modified iris spatula. The distance between the bottom of the micropocket and the limbus was about 1 mm. A prepared sterile Hydron pellet was rehydrated with a drop of sterile saline and placed into the corneal micropocket. The cornea was covered with gentamycin ophthalmic ointment (Alleran, Inc., Irvine, Calif.) after surgery. Rats were randomly divided into treated and control groups. Before administration, BTO-956 was suspended at 150 mg/mL in 0.5% methylcellulose in saline containing 0.1% Tween 80. The drug was administrated by oral gavage at a dose of 500 mg/kg body weight, twice a day for 6 days beginning from the first postoperative day. The controls received vehicle only, and body weights of all animals were monitored and recorded daily. On the seventh postoperative day, animals were anesthetized with nembutal (50 mg/kg) and the thoracic aorta was rapidly cannulated in a retrograde fashion with PE 100 tubing. An incision was made in the right auricle for drainage of blood and saline during flushing and 40–60 mL of saline was injected via the tubing to wash out the blood from the vessels in the upper part of the body until the eyes, ears and nose became pale. Then 10 mL of Higgins waterproof Indian ink (Sanford, Bellwood, Ill.) was injected via the tubing to visualize corneal vessels. The eyes were enucleated, fixed in 10% neutralized formaldehyde buffer, and the corneas were dissected and mounted on slides. Slide-mounted corneal images were taken by using a Carl Zeiss MPS intravital microscope (Carl Zeiss, Hanover, Md.) with a camera connected to a PC equipped with Scion Image software and a frame grabber (Scion Corporation, Frederick, Md.).

For the quantitative analysis of corneal neovascularization, various parameters of the corneal images were measured by an investigator who was unaware of the treatment protocol. The shortest distance between the implanted pellet and the limbus was marked as the midline and was measured. The arc along the limbus for the entire vascularized area was drawn and the length of the arc was measured. The circumference of this area was calculated by using the following equation: Circumference (in clock hours)=Arc length×360/πD/30, where D is the corneal diameter. The marked arc was evenly divided into six sections, distances between vessel tips and the limbus at the five intersection points of the arc were measured, and the average vessel length was calculated. The perpendicular distance between the tip of the longest vessel and the limbus (longest vessel length) was also measured. To measure the percent vascular volume (i.e., the vascular volume density), three circles with a diameter of 100 pixels were located between the pellet and the limbus on the midline in the second and the fifth sections, respectively. The total area of each circle (Area-T) and the area for vessels in each circle (total black pixels) were measured (Area-V). The vascular volume density was defined as the ratio of Area-V to Area-T. An average value from these three circles was obtained for each cornea. Total vascularized corneal area was also measured. Images were calibrated by measuring a micrometer image at the same magnification and zoom parameters.

B. The Dorsal Skin-Fold Window Chamber Assay.

Details of the design and the surgical technique used for the rat dorsal skin-fold window chamber assay have been described elsewhere (Pappenfuss et al., *Microvasc. Res.* 18:311–318 (1979)). Briefly, the anatomical midline of the dorsal skin flap of an anesthetized rat was sutured to a pair of C-clamps and a skin-fold was retracted from the body surface by hanging the C-clamp on a stage. A circle of 1 cm of skin on each side of the skin-fold was surgically removed leaving two layers of fascia containing a few microvessels. After a pair of window frames was mounted, a piece of a R3230Ac rat mammary carcinoma (about 0.5 mm$^3$) from a donor rat was implanted onto the fascia in the window and the chamber was sealed with glass cover slips. On the fourth postoperative day, all tumor-containing windows were evaluated using an intravital microscope. The viability of the tumor implants, vasculature morphology, and blood flow in each window were crudely scored with 1–3 points assigned to each category. Only those windows with more than 6 points on this scale were included for further study. In preliminary studies in untreated animals, we found that this selection procedure effectively eliminates chamber preparations that fail to grow tumors for various technical reasons. Tumor-window-bearing animals were randomly divided into treated and control groups that were stratified by the window scores. Treatment with BTO-956 was performed from the fifth to the eleventh postoperative day at the same doses as those described above for the corneal neovascularization assay. On day 12, the tumor windows were evaluated for the effect of the drug on tumor growth and vascularization. Images of whole tumors and tumor vasculature were obtained from four peripheral tumor areas, three to four central tumor areas, and from four areas in the surrounding granulating tissue, as described above. Again, measurements of various image parameters were made by an investigator who was unaware of the treatment protocol. Using the image analysis software, the cumulative length of all vessels in focus in each image was measured. Vascular length densities were calculated by dividing the total vessel length in a frame by the area of the frame. The diameters of all vessels in each image at high magnification were also measured and averaged.

C. Statistical Analysis.

All data were reported as means +/− the SEM for each group. The statistical significance of differences between treated and control groups was determined by using an unpaired t-test or the Mann-Whitney U-test. Statistically significant differences were defined as having a $p<0.05$.

D. Effect of BTO-956 on the Proliferation of R3230Ac Rat Mammary Carcinoma Cells.

To investigate the effect of BTO-956 on the proliferation of R3230Ac cells, they were first plated at $10^6$ cells/100-mm-diameter plastic culture dish in DMEM containing 10% fetal bovine serum (EBS; Sigma, St. Louis, Mo.) and 25 mM HEPES (pH 7.4), and incubated at 37° C. in 5% $CO_2$ for two days. Cells were then plated in a 96-well culture plate at $2\times10^3$ cells/well in 100 $\mu$l of DMEM-HEPES-10% FBS and incubated at 37° C. overnight. BTO-956 was added to the cells over the concentration range of 0–10 $\mu$M and they were incubated at 37° C. for three days. The effect of BTO-956 on the proliferation of the cells was measured on the fourth day by using the nontoxic redox-sensitive dye Alamar Blue in a calorimetric assay.

Results

No significant body weight loss or behavioral changes were found for any animals treated with BTO-956 in either study. This result concerning the safety of BTO-956 is consistent with those of previous in vivo studies showing that the drug is well tolerated by animals given similar doses by oral administration (Chen et al., *Bioch. Pharmacol.* 56:623–633 (1998)).

A. BTO-956 Inhibits Corneal Angiogenesis.

Figure 10:
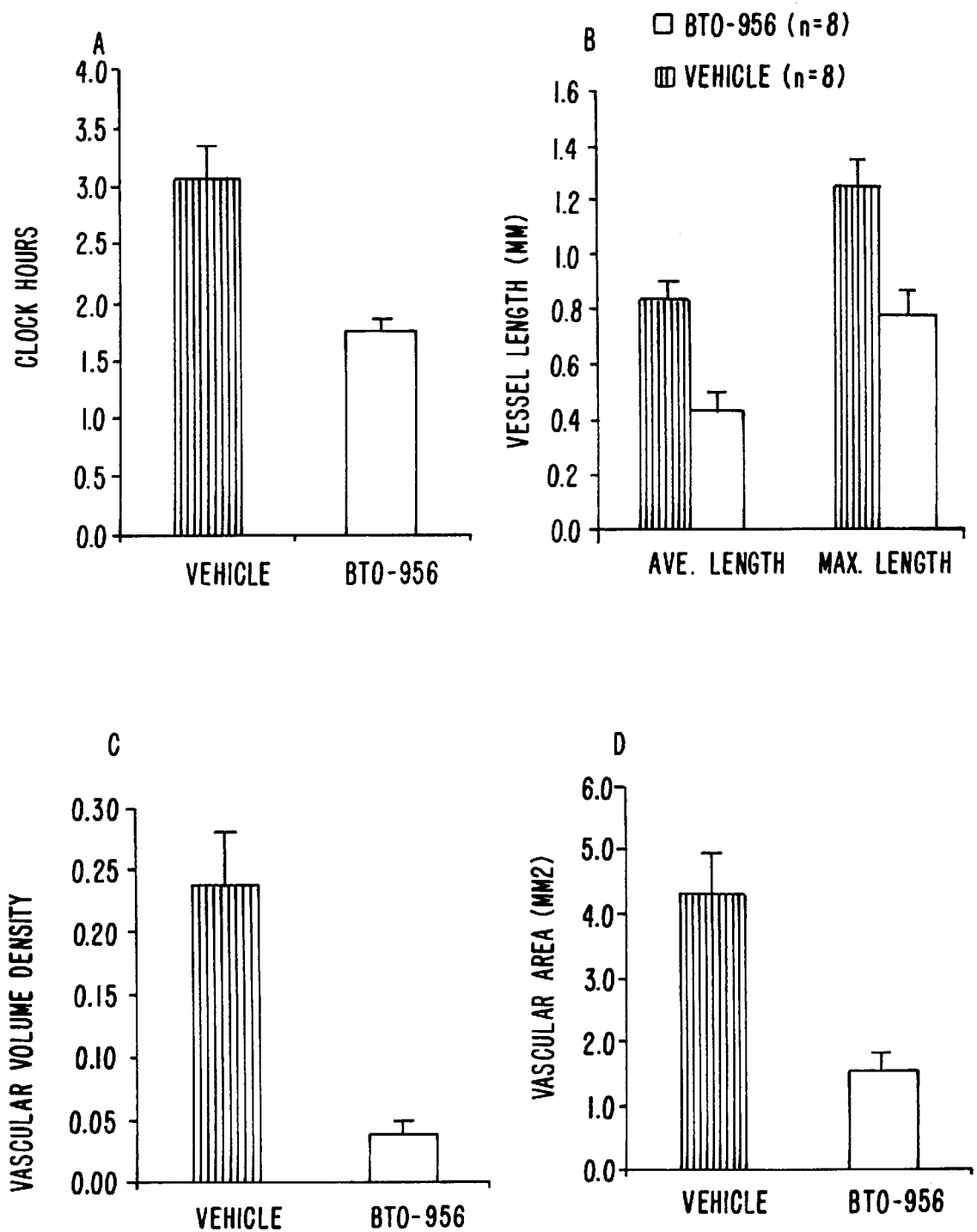
FIGS. 10(A–D) illustrate a quantitative comparison of corneal neovascularization induced by bFGF in Fischer 344 rats. All parameters associated with corneal neovascularization were significantly lower in BTO-956 treated animals compared with controls. The circumference values (clock hours) for corneal neovascularization in treated and control animals were 1.74±0.11 and 3.08±0.283 (p<0.01), respectively (Panel A). The average vessel lengths in treated and control animals were 0.42±0.07 mm and 0.84±0.07 mm, respectively (p<0.001). The maximum vessel lengths in treated and control animals were 0.76±0.09 mm and 1.24±0.09 mm, respectively (p<0.01) (Panel B). The vascular volume densities in treated and control animals were 0.037±0.01 and 0.24±0.042 (p<0.01), respectively (Panel C). The total vascular areas in treated and control animals were 1.52±0.27 mm and 4.34±0.61 mm² (p<0.01), respectively (Panel D). Error bars represent the standard error of the mean (SEM).

Corneal neovascularization induced by bFGF in BTO-956-treated animals was markedly reduced compared with vehicle-treated control animals. The pellet sizes and the distances between the pellet and the limbus for each group were similar. Quantitative comparison showed that all parameters relevant for measuring the extent of corneal neovascularization were significantly lower in BTO-956 treated animals compared with control animals. Thus, the circumference of neovascularization in treated rat corneas was reduced by 45% compared with controls ($p<0.01$, FIG. 10A). In addition, the average and maximum vessel lengths in treated animals were reduced by 50% ($p<0.001$) and 38% ($p<0.01$), respectively, relative to controls (FIG. 10B). Finally, the vascular volume density and the total vascular area were decreased by 84.5% ($p<0.01$, FIG. 10C) and 65% ($p<0.01$, FIG. 10D), respectively, compared with controls. Together, these findings demonstrate that BTO-956 given by oral administration can strongly inhibit mammalian angiogenesis induced by a pro-angiogenic factor.

B. BTO-956 Inhibits Tumor Growth and Angiogenesis.

Figure 11:
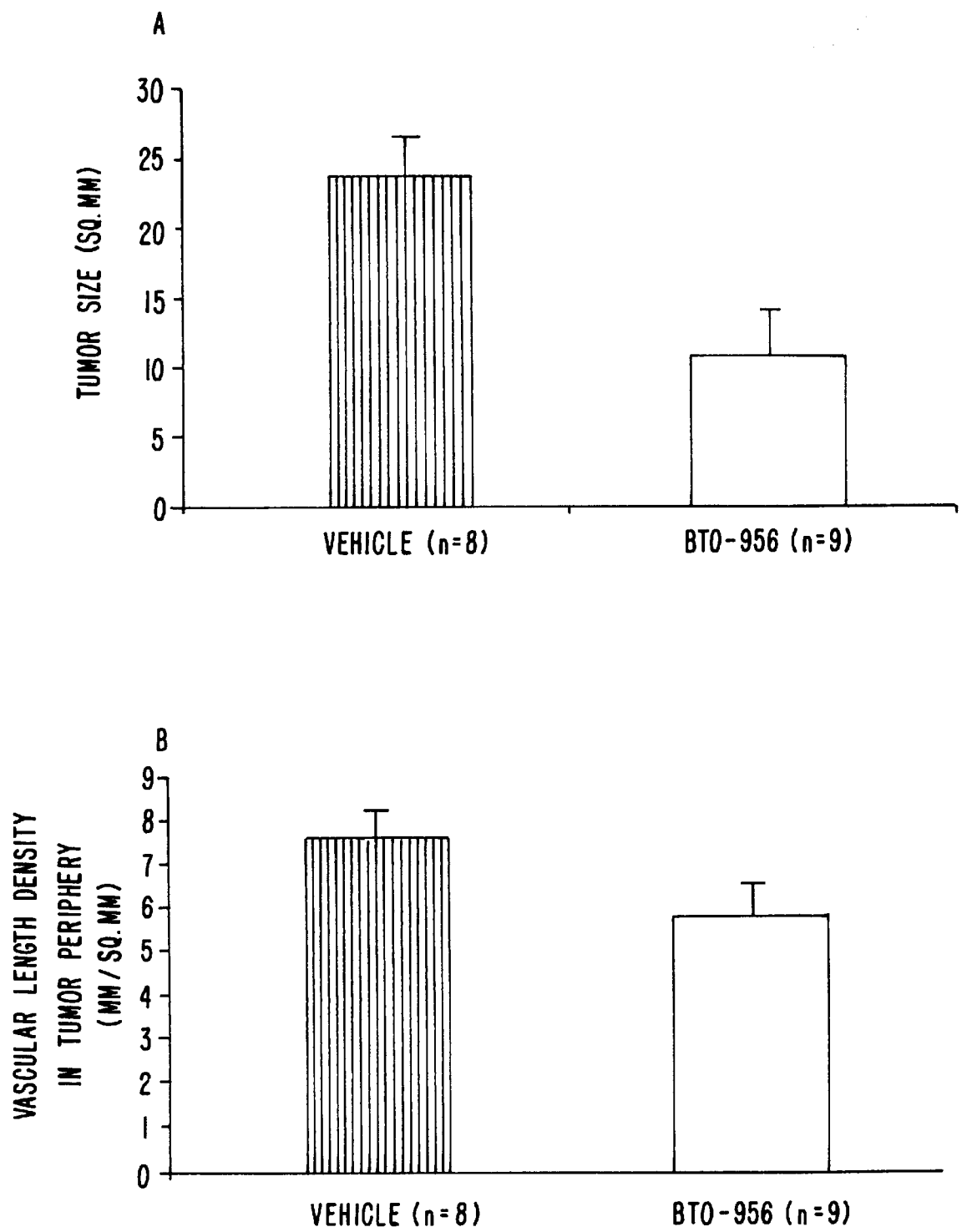
FIGS. 11(A–B) illustrate quantitative comparison of the effect of BTO-956 on the growth and neovascularization of the R3230Ac rat mammary carcinoma implanted in rat dorsal skin-fold window chambers in Fischer 344 rats. The average sizes of tumors in BTO-956 treated and control animals, as estimated by measurements of two-dimensional areas, were 10.79±3.35 mm² and 23.8±2.54 mm² (p<0.05), respectively (Panel A). The vascular length densities in the peripheral tumor zones in treated and control animals were 5.85±0.78 mm/mm² and 7.75±0.56 mm/mm², respectively (p<0.05) (Panel B). Error bars represent the standard error of the mean (SEM).

As described above, after establishment of the R3230 Ac rat mammary carcinoma tumors in dorsal skin-fold window chambers, BTO-956 was orally administered during post-operative days 5 to 11. In response to this treatment, the tumors growing in the windows of BTO-956 treated animals were much smaller than the control tumors. The treated tumors were also less vascularized, especially in the periphery where angiogenesis is prominent. Specifically, tumor areas were reduced more than 50% compared with controls in BTO-956 treated compared with control animals (23.8 2.54 $mm^2$ for treated animals, 10.79±3.35 $mm^2$ for controls; $p<0.05$; FIG. 11A). The vascular length density in peripheral tumor areas in BTO-956-treated animals was significantly less than that of the controls (5.2±0.95 $mm/mm^2$ for treated animals. 7.75±0.56 $mm/mm^2$ for controls: $p<0.05$; FIG. 11B). In contrast, there was no significant difference in the vascular length density between treated and control groups in either the central tumor areas (3.26±0.81 $mm/mm^2$ for treated animals, 4.17±0.23 $mm/mm^2$ for controls) or in the surrounding granulating tissue (8.71±1.05 $mm/^2$ for treated animals, 8.69±0.83 $mm/mm^2$ for controls). The vascular diameter in the central tumor areas was larger than that in peripheral tumor areas in both groups. However, there were no significant differences in vascular diameter between the two groups in the peripheral tumor areas (32.19±4.46 $\mu$m for treated animals, 36.24±5.28 $\mu$m for controls), the central tumor areas (35.84±9.63 $\mu$m for treated animals, 32.03±4.43 $\mu$m for controls), or in surrounding areas (21.52±3.33 $\mu$m for treated animals, 19.17±1.43 $\mu$m for controls). Together, these findings demonstrate that BTO-956 given by oral administration can strongly inhibit angiogenesis in the periphery of a solid tumor where the most active neovascularization occurs.

C. Effect of BTO-956 on the Proliferation of R3232Ac Tumor Cells in vitro.

Figure 12:
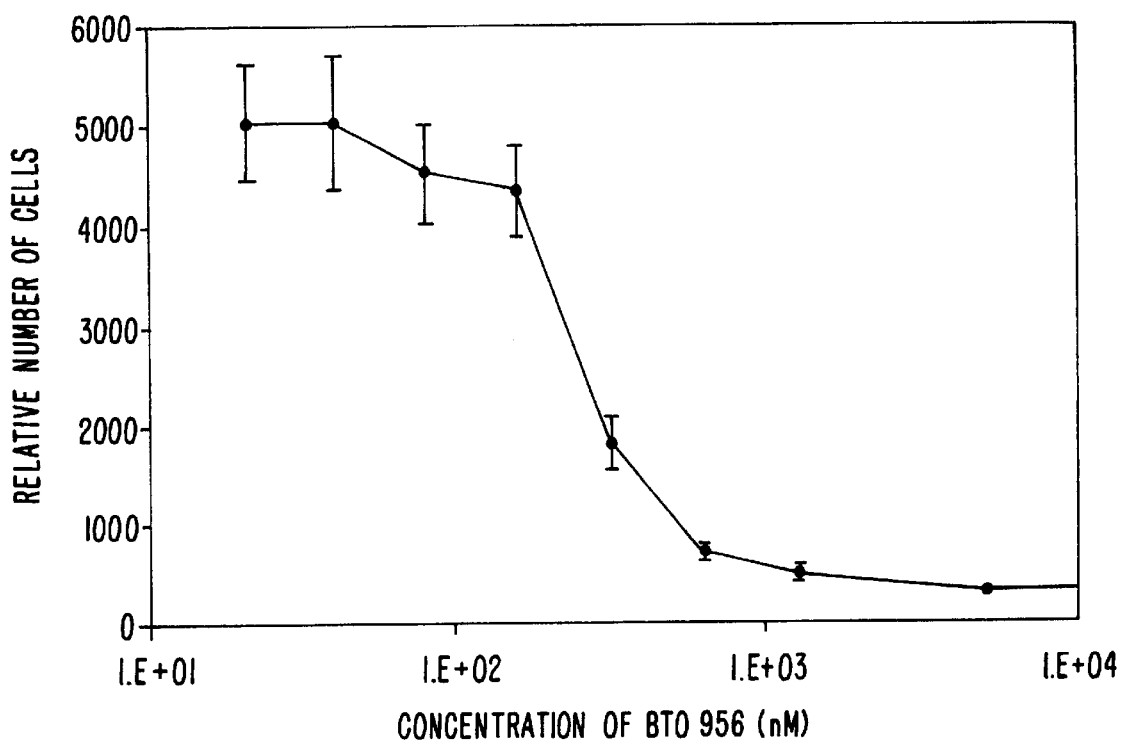
FIG. 12 illustares the effect of BTO-956 on the proliferation of R3230Ac rat mammary carcinoma cells in vitro. Error bars represent standard deviations (SD).

FIG. 12 shows that BTO-956 inhibited the in vitro proliferation of R3230Ac cells with an $ID_{50}$(the dose required to decrease the number of cells by 50% relative to the control) of approximately 250 nM. Using the same in vitro assay, it was determined that BTO-956 also inhibited the proliferation of normal human microvascular endothelial cells (HMVECs; obtained from dermis; Clonetics Corporation, Walkersville, Md.) with an $ID_{50}$ of approximately 200 nM. Therefore, BTO-956 can inhibit the proliferation of both tumor cells and normal microvascular endothelial cells. Together, these findings indicate that BTO-956 is cytotoxic or cytostatic toward both transformed and normal cell compartments of a solid tumor.

Discussion

This study demonstrates that oral administration of the tubulin-binding drug BTO-956 inhibited (1) bFGF-induced rat corneal neovascularization and (2) tumor growth and angiogenesis of the R3230Ac rat mammary carcinoma. The anti-angiogenic activity of BTO-956 was detectable in the peripheral areas of these implanted tumors where the most active angiogenesis occurs (see, Suzuki et al., *Jpn. J. Cancer Res.* 90:1387–95 (1999); Fukumura et al., *Cell* 94:715–25 (1998)). BTO-956 has the ability to disrupt cellular microtubule dynamics and can be a potent antivascular or anti-angiogenic agent. The molecular mechanism of this anti-angiogenic effect of BTO-956 is presently unknown. However, because BTO-956 can strongly inhibit the proliferation of both R3230Ac tumor cells and normal microvascular endothelial cells in vitro, it is likely that its ability to inhibit both corneal and tumor angiogenesis involves an effect on endothelial cell proliferation and survival. BTO-956 can arrest proliferating tumor cells at a $G_2$/M checkpoint and cause apoptosis, similar to the effect of other tubulin-binding agents such as colchicine, vinblastine, and paclitaxel.

BTO-956 has a structure similar to that of combretastatin A-4 (CSA-4), and both of these molecules bind to colchicine sites on β-tubulin. The findings from the corneal neovascularization assay reported here suggest that BTO-956 is likely to function as an anti-antiogenic agent.

The results from the tumor window chamber assay for the R3230Ac rat mammary carcinoma provide a further demonstration that BTO-956 inhibits tumor growth. Thus, two-dimensional areas of this tumor type were decreased by more than 50% compared with the areas of the control tumors. Indeed, if the volume of these tumors were considered, this antitumor effect of BTO-956 would be significantly greater. Other studies have demonstrated that the angiogenic activity in experimental tumors is greatest in peripheral zones (see, Suzuki et al., *Jpn. J. Cancer Res.* 90:1387–95 (1999); Fukumura et al., *Cell* 94:7 15–25 (1998)). Consistent with this conclusion, the results reported here show that the vascular length density in the periphery of the R3230Ac tumor was significantly decreased in the window chambers of BTO-956 treated animals, whereas the vascular length density in central areas of these tumors was unchanged. These findings indicate that the anti-angiogenic effect of BTO-956 is most potent in actively growing areas of a tumor. No serious toxic effects of the drug on tumor-bearing animals such as weight loss or behavioral abnormalities, even at orally administered doses as high as 500 mg/kg per day given daily for up to seven days. These findings indicate that BTO-956 can be administrated orally with considerable safety and suggest that it has promise for eventual clinical applications.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method for treating an inflammatory disease, said method comprising administering to an individual having an inflammatory disease a therapeutically effective amount of a compound having the formula:

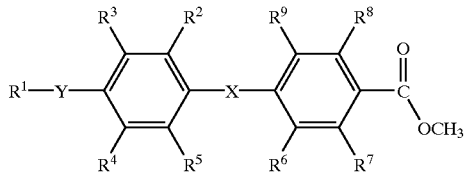

or a pharmaceutically acceptable salt thereof;
wherein:
$R^1$ is $C_1$–$C_6$-alkyl;
$R^2$, $R^3$, $R^4$ and $R^5$ are each independently selected from the group consisting of hydrogen, $C_1$–$C_5$-alkyl, $C_2$–$C_6$-alkynyl, aryl, hydroxyl, $C_1$–$C_6$-alkoxy, halogen, $NO_2$, and $NH_2$;
$R^6$, $R^7$, $R^8$ and $R^9$ are each independently selected from the group consisting of hydrogen, $C_1$–$C_6$-alkyl, $C_2$–$C_6$-alkynyl, aryl, hydroxyl, $C_1$–$C_6$-alkoxy, halogen, $NO_2$ and $NH_2$;
Y is a heteroatom; and
X is selected from the group consisting of a bond, oxygen, sulfur, —$CH_2$— and carboxy.

2. The method in accordance with claim 1, wherein $R^1$ is methyl or ethyl;
$R^2$, $R^3$, $R^4$ and $R^5$ are each independently selected from group consisting of hydrogen, $C_1$–$C_4$-alkyl, $C_2$–$C_4$-alkenyl, $C_2$–$C_4$-alkynyl, aryl, hydroxyl, $C_1$–$C_4$-alkoxy, halogen, $NO_2$ and $NH_2$;
$R^6$, $R^7$, are each independently selected from the group consisting of hydrogen, $C_1$–$C_4$-alkyl, $C_2$–$C_4$-alkenyl, $C_2$–$C_4$-alkynyl, aryl, hydroxyl, $C_1$–$C_4$-alkoxy, halogen, $NO_2$ and $NH_2$;
$R^8$ and $R^9$ are iodine; and
X is selected from the group consisting of a bond, oxygen, sulfur, —$CH_2$— and carboxy.

3. The method in accordance with claim 1, wherein the compound is methyl-3,5-diiodo-4-(4'-methoxyphenoxy) benzoate.

4. The method in accordance with claim 1, wherein said inflammatory disease is centralized in a tissue or organ.

5. The method in accordance with claim 1, wherein said compound is formulated in a pharmaceutically acceptable form with an excipient or carrier.

6. The method in accordance with claim 1, wherein said compound is formulated in a liposome.

7. The method in accordance with claim 6, wherein said liposome is conjugated to a targeting moiety which is specific for endothelial cells.

8. The method in accordance with claim 1, wherein said inflammatory disease is an inflammatory bowel disease.

9. The method in accordance with claim 8, wherein said inflammatory bowel disease is selected from the group consisting of Crohn's disease and ulcerative colitis.

10. The method in accordance with claim 1, wherein said inflammatory disease is selected from the group consisting of psoriasis, sarcoidosis and rheumatoid arthritis.

11. The method in accordance with claim 1, wherein said inflammatory disease is in a human being.

12. A method of inhibiting granulomas, said method comprising contacting a tissue or organ having said granulomas with an inhibiting amount of a compound having the formula:

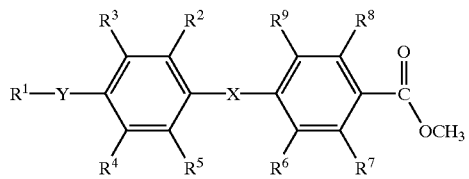

or a pharmaceutically acceptable salt thereof;
wherein:
$R^1$ is $C_1$–$C_6$-alkyl;
$R^2$, $R^3$, $R^4$ and $R^5$ are each independently selected from group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$ and $NH_2$;
$R^6$, $R^7$, $R^8$ and $R^9$ are each independently selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$ and $NH_2$;
Y is a heteroatom; and
X is selected from the group consisting of a bond, oxygen, sulfur, —$CH_2$— and carboxy.

13. The method in accordance with claim 12, wherein $R^1$ is methyl or ethyl;

R², R³, R⁴ and R⁵ are each independently selected from group consisting of hydrogen, $C_1$–$C_4$-alkyl, $C_2$–$C_4$-alkenyl, $C_2$–$C_4$-alkynyl, aryl, hydroxyl, $C_1$–$C_4$-alkoxy, halogen, $NO_2$ and $NH_2$;

R⁶, R⁷, are each independently selected from the group consisting of hydrogen, $C_1$–$C_4$-alkyl, $C_2$–$C_4$-alkenyl, $C_2$–$C_4$-alkynyl, aryl, hydroxyl, $C_1$–$C_4$-alkoxy, halogen, $NO_2$ and $NH_2$;

R⁸ and R⁹ are iodine; and

X is selected from the group consisting of a bond, oxygen, sulfur, —$CH_2$— and carboxy.

14. The method in accordance with claim 12, wherein the compound is methyl-3,5-diiodo-4-(4'-methoxyphenoxy) benzoate.

15. The method in accordance with claim 12, wherein said granuloma is in a mammalian subject.

16. The method in accordance with claim 12, wherein said compound is formulated in a pharmaceutically acceptable form with an excipient or carrier.

17. The method in accordance with claim 12, wherein said compound is formulated in a liposome.

18. The method in accordance with claim 17, wherein said liposome is conjugated to a targeting moiety which is specific for endothelial cells.

19. A method for prophylactically treating inflammation, said method comprising administering to an individual who has come in contact with an agent of inflammation a therapeutically effective amount of a compound having the formula:

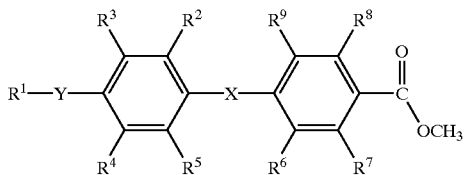

or pharmaceutically acceptable salt thereof;

wherein:

R¹ is $C_1$–$C_6$-alkyl;

R², R³, R⁴ and R⁵ are each independently selected from the group consisting of hydrogen, $C_1$–$C_5$-alkyl, $C_2$–$C_6$-alkynyl, aryl, hydroxyl, $C_1$–$C_6$-alkoxy, halogen, $NO_2$, and $NH_2$;

R⁶, R⁷, R⁸ and R⁹ are each independently selected from the group consisting of hydrogen, $C_1$–$C_6$-alkyl, $C_2$–$C_6$-alkynyl, aryl, hydroxyl, $C_1$–$C_6$-alkoxy, halogen, $NO_2$ and $NH_2$;

Y is a heteroatom; and

X is selected from the group consisting of a bond, oxygen, sulfur, —$CH_2$— and carboxy, thereby prophylactically treating inflammation.

20. The method in accordance with claim 19, wherein said compound is methyl-3,5-diiodo-4-(4'-methoxyphenoxy) benzoate.

* * * * *